US011625093B2

(12) United States Patent
Ehrlich

(10) Patent No.: US 11,625,093 B2
(45) Date of Patent: Apr. 11, 2023

(54) DEVICE, METHOD, AND SYSTEM OF HIGH-SPEED EYE TRACKING

(71) Applicant: Sharon Ehrlich, Zoran (IL)

(72) Inventor: Sharon Ehrlich, Zoran (IL)

( * ) Notice: Subject to any disclaimer, the term of this patent is extended or adjusted under 35 U.S.C. 154(b) by 137 days.

(21) Appl. No.: 16/962,526

(22) PCT Filed: Jan. 24, 2019

(86) PCT No.: PCT/IL2019/050101
§ 371 (c)(1),
(2) Date: Jul. 16, 2020

(87) PCT Pub. No.: WO2019/145954
PCT Pub. Date: Aug. 1, 2019

(65) Prior Publication Data
US 2020/0348754 A1 Nov. 5, 2020

Related U.S. Application Data

(60) Provisional application No. 62/621,643, filed on Jan. 25, 2018.

(51) Int. Cl.
*G06F 3/01* (2006.01)
*H05B 47/155* (2020.01)
(Continued)

(52) U.S. Cl.
CPC ............ *G06F 3/013* (2013.01); *H05B 45/22* (2020.01); *H05B 47/155* (2020.01);
(Continued)

(58) Field of Classification Search
CPC ....... G06F 3/013; H05B 47/155; H05B 45/22; A61B 3/0008; A61B 3/113; A61B 2503/12
See application file for complete search history.

(56) References Cited

U.S. PATENT DOCUMENTS

| 7,401,920 B1 * | 7/2008 | Kranz | G02B 27/0093 |
| | | | 382/117 |
| 10,011,216 B1 * | 7/2018 | Rovik | G06V 20/588 |

(Continued)

FOREIGN PATENT DOCUMENTS

WO 2014/209816 A1 12/2014

OTHER PUBLICATIONS

International Search Report (ISR) in PCT/IL2019/050101, dated Jun. 11, 2019.
(Continued)

*Primary Examiner* — Amare Mengistu
*Assistant Examiner* — Gloryvid Figueroa-Gibson
(74) *Attorney, Agent, or Firm* — Browdy and Neimark, P.L.L.C.

(57) ABSTRACT

Device, method, and system of high-speed eye tracking. A system includes: a set of illumination sources, to selectively generate illumination pulses towards a human eye in accordance with a particular timing scheme per illumination source and in accordance with a particular wavelength per illumination source; a set of optical sensors, to sense changes to one or more properties of reflections of the illumination pulses from the human eye in response to modifications in operational properties of the illumination sources; and a processor to process the sensed changes, and to generate one or more processing results that are based on the sensed changes.

32 Claims, 9 Drawing Sheets

(51) Int. Cl.
*H05B 45/22* (2020.01)
*A61B 3/00* (2006.01)
*A61B 3/113* (2006.01)

(52) U.S. Cl.
CPC .............. *A61B 3/0008* (2013.01); *A61B 3/113* (2013.01); *A61B 2503/12* (2013.01)

(56) References Cited

U.S. PATENT DOCUMENTS

| | | | |
|---|---|---|---|
| 2002/0013573 A1* | 1/2002 | Telfair | A61B 3/113 606/5 |
| 2008/0013574 A1* | 1/2008 | Furuya | H01S 3/0675 348/E9.026 |
| 2014/0375541 A1* | 12/2014 | Nister | A61B 3/113 345/156 |
| 2016/0081556 A1* | 3/2016 | Dreher | A61B 5/6821 600/407 |
| 2016/0353025 A1 | 12/2016 | Eskilsson | |
| 2020/0026349 A1* | 1/2020 | Fontanel | G06V 40/19 |

OTHER PUBLICATIONS

Written Opinion of the International Searching Authority in PCT/IL2019/050101, dated Jun. 11, 2019.

\* cited by examiner

Stimuli and Measurement

Remote Light & Sensing

DEVICE, METHOD, AND SYSTEM OF HIGH-SPEED EYE TRACKING

CROSS-REFERENCE TO RELATED APPLICATIONS

This patent application is a National Stage of PCT international application number PCT/IL2019/050101, having an international filing date of Jan. 24, 2019, published as international publication WO 2019/145954 A1, which is hereby incorporated by reference in its entirety; which claims priority and benefit from U.S. 62/621,643, filed on Jan. 25, 2018, which is hereby incorporated by reference in its entirety.

FIELD

The present invention is related to vision sensors and eye tracking systems.

BACKGROUND

Millions of people utilize mobile and non-mobile electronic devices, such as smartphones, tablets, laptop computers and desktop computers, in order to perform various activities. Such activities may include, for example, browsing the Internet, sending and receiving electronic mail (email) messages, taking photographs and videos, engaging in a video conference or a chat session, playing games, or the like.

Some smartphones include a camera able to capture images and videos, and a processor able to determine whether the user is actually looking at the screen of the smartphone. For example, in a "smart stay" feature of some smartphones, if it is determined that the user is looking at the screen, then the screen remains active regardless of a screen timeout setting of the smartphone. Similarly, in a "smart pause" feature of some smartphones, playback of a video is automatically paused upon detection that the user is not looking at the screen.

SUMMARY

The present invention may include, for example, systems, devices, and methods for high-speed tracking or monitoring of the eye or of a pair of eyes, and/or of particular regions or portions or components of an eye (e.g., the pupil, the cornea, the sclera, the iris), and/or of changes or modifications in the location and/or size and/or movement of such eye-portions or eye-components, and/or of properties or characteristics of such components and/or related to such components (e.g., direction of a gaze; change in direction of gaze; blinking), and/or detailed dynamics of eye parameters and/or eye movement and/or pupil movement and/or eye-component movement.

The present invention may provide other and/or additional benefits or advantages.

DETAILED DESCRIPTION OF SOME DEMONSTRATIVE EMBODIMENTS OF THE PRESENT INVENTION

Figure 1:
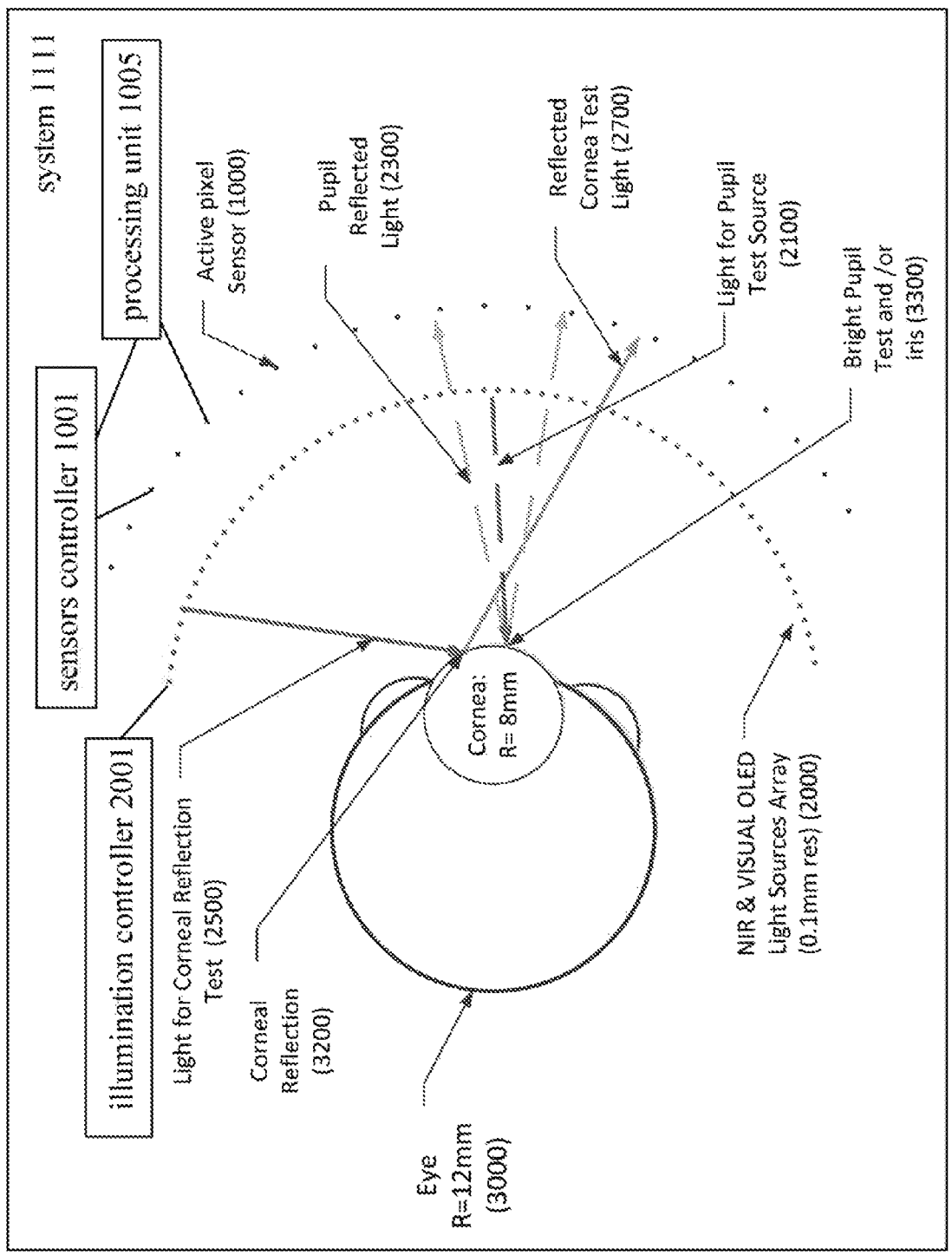
FIG. 1 is a schematic illustration of a system, in accordance with some demonstrative embodiments of the present invention.

The present invention comprises devices, systems, and methods of rapid and reliable tracking and/or measurement of detailed dynamics of eye parameters and/or eye movement, at high resolution.

In some embodiments, optionally, visual stimulation may be generated and/or displayed to the eye, and the reaction or response to such stimulation (e.g., physiological reaction, cognitive reaction) is sensed, detected and/or measured.

The present invention utilizes detection and/or measurement of changes, which are sensed or detected by a set or array or matrix or batch of detectors or sensors, the changes being one or more of: changes in illumination or light that is reflected towards or that reaches such detectors or sensors which are sensitive to rapid changes of light and/or to rapid movement or displacement of a light-source and/or to rapid movement or displacement of an object (e.g., the eye) from which the light is reflected and/or to rapid movement or displacement of the sensors or detectors themselves; wherein such detectors or sensors are sensitive to one or more of such changes in combination with movement of the eye (or eye component) itself, and not only based on passive detection of the eye movement by itself. The system of the present invention generates pre-programmed and/or pre-calculated rapid and/or spatial changes in the illumination-based stimuli or in the light-based stimuli to the eye, optionally utilizing one or more suitable frequency and/or wave-length values or ranges; and optionally utilizes a set of active wide-range or ultra-wide-range sensors optionally having high Signal to Noise Ratio (SNR) and having a very short response-time to such change(s).

In some embodiments, the illumination sources are selectively activated and de-activated, at a particular wavelength or at different particular wavelengths; for example, a first illumination source is activated at time point T1 with wavelength W1 and is de-activated at time point T2; whereas, a second illumination source is activated at time point T3 with wavelength W2 and is de-activated at time point T4. In some embodiments, the time-slot of T2-T1 is equal to the time-slot of T4-T3. In other embodiments, the time-slot of T2-T1 is different from the time-slot of T4-T3. In some embodiments, the timing scheme is pre-programmed or pre-configured. In other embodiments, at least a portion of the timing scheme is dynamically modified and/or dynamically configured, based on the sensed response to the sensed reaction of one or more ocular components to a previous (or to several previous) illumination(s).

Accordingly, instead of utilizing a frame-based or frames-based camera or imager, which capture an entire image of an entire region or area-of-interest regardless of whether a portion of the region changed or did not change, the system of the present invention utilizes a set of sensors or detectors such as Active Pixel sensors, that react or respond only to a change, or that generate an output signal on a pixel-by-pixel basis in an a-synchronous (non-synchronous) manner only upon detection of a change in a particular pixel; thereby enabling to perform very rapid sampling, by utilizing and/or analyzing (and optionally, transmitting or transferring to a remote recipient or to a local recipient unit or processor) only a reduced amount of data (e.g., representing only pixels that changed, and only upon their change), and thereby enabling rapid and reliable real-time processing and analysis of such data.

The present invention thus enables rapid measurement at high resolution of small-size yet rapid changes or displacements, which conventional eye tracking systems are not capable of detecting and/or measuring. Some of the parameters that are tracked and/or detected are, for example, location and/or size and/or displacement and/or movement of the pupil; location and/or size and/or displacement and/or movement of the cornea; the movement of one eye-component relative to another eye-component (e.g., the movement of the pupil relative to the iris); saccades; micro-saccades; post saccadic oscillations; blinks; and/or other suitable parameters.

The present invention may comprise a variety of implementations; for example, as part of an aircraft (e.g., for tracking the eye(s) of a pilot), as part of a vehicle (e.g., for tracking the eye(s) of the driver), as part of a vessel or other means of transportation (e.g., for tracking the eye(s) of the operator), as part of a gaming system or gaming console (e.g., for tracking the eye(s) of a user or a "gamer"), as part of a multimedia system or an audio/video playback system (e.g., for tracking the eye(s) of the viewer), as part of an advertising system (e.g., for tracking the eye(s) of a viewer or a consumer), as part of a medical device or a medical system (e.g., for detecting or measuring or treating a medical condition of an eye of a patient; or as part of an endoscope or catheter or guide-wire or stent, or as part of a capsule endoscopy device or a swallowable "pill camera" device), as part of a teaching or learning system (e.g., for tracking the eye movements of students in a classroom or of students of an online lesson or online course), as part of a testing system or assessment system (e.g., for tracking the eye movements of a student or person that is taking an examination or assessment or test), or as part of other suitable systems.

Optionally, some embodiments may generate different types of visual stimuli that are projected towards the eye, during in the measurement and sensing process, and without interrupting such measurement and without interfering with such measurement; and further enable to measure the reaction or the response to such stimuli, directly and without requiring a synchronization channel. Some embodiments of the present invention may thus be configured to construct a profile of characteristics of the response to such generated stimuli, and to detect one or more conditions or insights that can be deduced from such characteristics; for example, to determine that a pilot or a driver is tired or is not alert or is drunk or is drugged or is suffering from a medical condition, to determine that a user is subject to stress or pressure, or the like.

Some embodiments may perform one or more of the following processes, or a combination of these processes: rapid modulation or modification of the illumination system that illuminates or projects light towards the eye, such as by generating rapid vibrations or oscillations of the illumination system (e.g., at a small amplitude), along one axis or along two axes or along three axes; and/or, by generating rapid vibrations or oscillations of the detectors/sensors (e.g., at a small amplitude), along one axis or along two axes or along three axes. In some embodiments, the time-period for performing one operation of vibration or one cycle of oscillation, is smaller than the smallest time-period that a human eye requires in order to physically perform any type of modification (e.g., pupil movement, blink, or the like); such that the vibration or oscillation further enables the system of the present invention to detect, and not to miss, any change or movement in any eye-component of a human user.

Reference is made to FIG. 1, which is a schematic illustration of a system 1111, in accordance with some demonstrative embodiments of the present invention. For example, a set of illumination sources 2000 and a set of active pixel sensors 1000 are positioned and/or located in proximity to (or directed towards) a human eye 3000.

The set of illumination sources 2000 comprises, for example, a group or batch or matrix or array or a pattern of multiple Light Emitting Diode (LED) units, for example, multiple LEDs or multiple Organic LEDs (OLEDs). The set of illumination sources is able to generate light or electromagnetic radiation, at one or more frequencies or wavelengths or ranges-of-wavelengths; e.g., visible light; non-visible light; infrared light having wavelength of 700 or more nanometers; near infrared (NIR) light having wavelength of 700 to 1,200 nanometer; infrared light that is non-NIR light such as having wavelength of 1,200 nanometers or more; or the like.

The operation of the set of illumination sources 2000 is controlled, modified and/or regulated by an illumination controller 2001. For example, rapid and short light-pulses are generated, in the NIR spectrum, each light-pulse being illuminated (being activated) for approximately 3 or 5 or 8 or 10 microseconds; at a rapid rate or at short time intervals (e.g., approximately 4 or 6 or 12 microseconds between two light pulses). Such light-pulses cause or trigger a reaction or a response or a reflection (partial reflection or entire reflection) from one or more areas-of-interest in the eye, or from one or more eye components; and such reaction or response or reflected light is then captured by and/or detected by the set of sensors 1000.

In some embodiments, all of the illumination sources 2000 are activated (illuminate) at the same time, and all of them are non-activated at the same time. In other embodiments, a first group of illumination sources is activated, while at the same time a second group of illumination sources is non-activated; and vice versa. In still other embodiments, different groups of illumination sources are alternating between being activated and being non-activated; optionally with a short idle period between activations of groups of illumination sources. In yet other embodiments, at least one of the illumination sources is activated and illuminating, while at least one other illumination source is non-activated and non-illuminating. In still other embodiments, at least two illumination sources are activated in two different time-slots that do not have any overlapping time-period. In yet other embodiments, at least two illumination sources are activated in two different time-slots that do share an overlapping time period.

In some embodiments, all the illumination sources 2000 are directed towards a particular spatial point or towards a particular spatial area (e.g., corresponding to an area in which a human eye is known to be or is estimated to be). In other embodiments, at least two of the illumination sources 2000 are directed towards two different spatial points or spatial areas. In still other embodiments, at least two of the illumination sources are directed to illuminate two different spatial areas-of-interest that do not share any overlapping area. In yet other embodiments, at least two of the illumination sources are directed to illuminate to different spatial areas-of-interest that do share a particular overlapping area.

The set of sensors 1000 are active pixels sensors, which are independent of each other and are a-synchronic of non-synchronic with each other. They do not require the system to capture an entire frame of multiple pixels at fixed time intervals. Rather, each pixel is captured autonomously and separately from neighboring and/or other pixels in the area-of-interest; and particularly, a pixel is captured, or a change in the illumination property of a pixel is captured or is signaled as output, only upon detection that such change has indeed occurred to that particular pixel.

In some embodiments, the set of sensors 1000 is associated with a sensors controller 1001, able to control or set or modify or regulate the operation of each one of the sensors. Optionally, the sensors controller 1001 may be implemented as a set of discrete or separate sensor controllers, such that each sensor controller is able to control a particular, discrete, sensor that is configured to sense and to signal changes in a particular pixel or a particular spatial area-of-interest that corresponds to a single pixel.

In some embodiments, each sensor may have a local processing capability, or may be associated with a local processor (e.g., optionally implemented as part of the sensor controller 1001), which is able to determine whether a change in the illumination property of the relevant single pixel has occurred or has not occurred, and able to output a signal (e.g., a True signal or a "1" value) if, and only if, and only when, such change is detected.

In some embodiments, each active pixel sensor may further have (by itself, and/or in combination with its sensor controller or processor) the capability to self-learn, and/or to self-adjust to, ambient and/or environmental systems; and the capability to self-correct or self-calibrate or self-configure its operational properties (e.g., its sensitivity threshold value, or its detection threshold value), based on the actual current conditions. In some embodiments, a separate calibration unit or configuration unit may operate to dynamically configure the sensitivity levels of particular sensor(s); for example, increasing the sensitivity level of sensor(s) when it is detected that the user is located in a bright surrounding, or decreasing the sensitivity level of sensor(s) when it is detected that the user is located in a dark surrounding, or the like.

In some embodiments, each active pixel sensor has a wide or very-wide dynamic range; for example, between 110 db to 150 db, or between 120 db to 150 db, or between 130 db to 148 db, or between 140 db to 145 db, or approximately 140 db, or approximately 143 db. Other suitable values or ranges may be used.

Each active pixel sensor responds rapidly to a change in the monitored pixel; for example, within 1 or 2 or 3 or 5 microseconds of the occurrence of such change; and generates an output signal indicating the change. The output signals from each such active pixel sensor, are transferred separately and in a non-synchronic manner, and not at pre-defined time intervals, and not at pre-defined "frame capture rate", to a processing unit 1005 which is able to process the incoming and a-synchronous data in real-time or in near-real-time. The processing unit 1005 need not wait to receive a full frame of pixels that is transferred at pre-defined and fixed time intervals. Accordingly, the system of the present invention needs to transfer less data (e.g., since only data of changed-pixels is transferred; and data of non-changed pixels is not transferred), and/or needs to perform less data-transfer events (e.g., since only upon a change in the value of a pixel, the transfer of data is made), and/or needs to process less data (e.g., no need to process data that corresponds to non-changed pixels), and/or is able to operate on a-synchronous data at it is being detected and signaled.

The system operates by activating and de-activating the illumination sources 2000, at particular time-spots and for particular time-lengths, and optionally at a particular illumination intensity, to generate particular light-pulses that are directed from the illumination sources 2000 towards the eye of the user and/or towards a particular area-of-interest of the eye (e.g., cornea, pupil), and/or that are reflected back (partially or entirely) from such eye-component or area-of-interest. For example, there is shown a generated ray of light 2500 (or, a stimulus ray of light) generated by an illumination unit and transmitted towards the cornea; and there is shown a reflected ray of light 2700 that is reflected back from the cornea at cornea point 3200.

Based on the known location or spatial location of the illumination sources 2000 and the sensors 1000 (such knowledge may be pre-known, or pre-configured, or hard-wired, or may be self-learned or deduced by the system itself). Based on the signals generated by one or more of the active pixel sensors 1000, and optionally by performing calculation operations on such signals and their spatial location and timing (e.g., optionally including statistical distribution analysis of the reflected signals), one or more of the parameters of interest are determined.

In some embodiments, the system may perform a set of operations in order to detect, measure, locate and/or track a particular eye-component such as the cornea (or pupil, or other component or region-of-interest or area-of-interest). For example, one or more particular illumination sources (e.g., in the Near InfraRed (NIR) range) are activated to generate a "test" light-ray or light-beam 2500, that is directed towards the eye; and the cornea reflects a reflected light-ray or light-beam 2700 from a corneal reflection point, and arrives to (and is sensed by or detected by) one or more of the active pixel sensors. Then, that illumination source(s) is (or are) de-activated; and a different illumination source (or, a different group of illumination sources) is activated, to similarly direct a different light-beam towards the eye, which is also reflected towards the same or other sensor(s). A plurality of such sets of selective illuminations and corresponding detections of their reflections, enable the system to measure the size, location, movement, and/or other properties of the cornea A similar process may be performed, for example separately (e.g., during a different time-slot) in order to characterize the pupil of the eye. For example, a light-ray or light-beam 2100 is generated by one or more of the illumination sources; it hits the pupil; and it is reflected back towards one or more sensors, as a reflected light-beam 2300 or reflected light-ray.

A similar process may be performed, for example separately (e.g., during a different time-slot) in order to characterize the bright portion of the pupil of the eye or to characterize the iris. For example, a light-ray or light-beam 2100 is generated by one or more of the illumination sources; it hits the iris or the bright portion of the pupil; and it is reflected back towards one or more sensors, as a reflected light-beam 3300 or reflected light-ray.

Some embodiments may thus utilize a set of illumination/detection cycles or iterations, in order to identify and detect the boundaries or border of an eye-component, and/or in order to characterize one or more properties of such eye-component, its size, location, position, orientation, movement, displacement, movement speed, acceleration, deceleration, shape, or the like.

Figure 2:
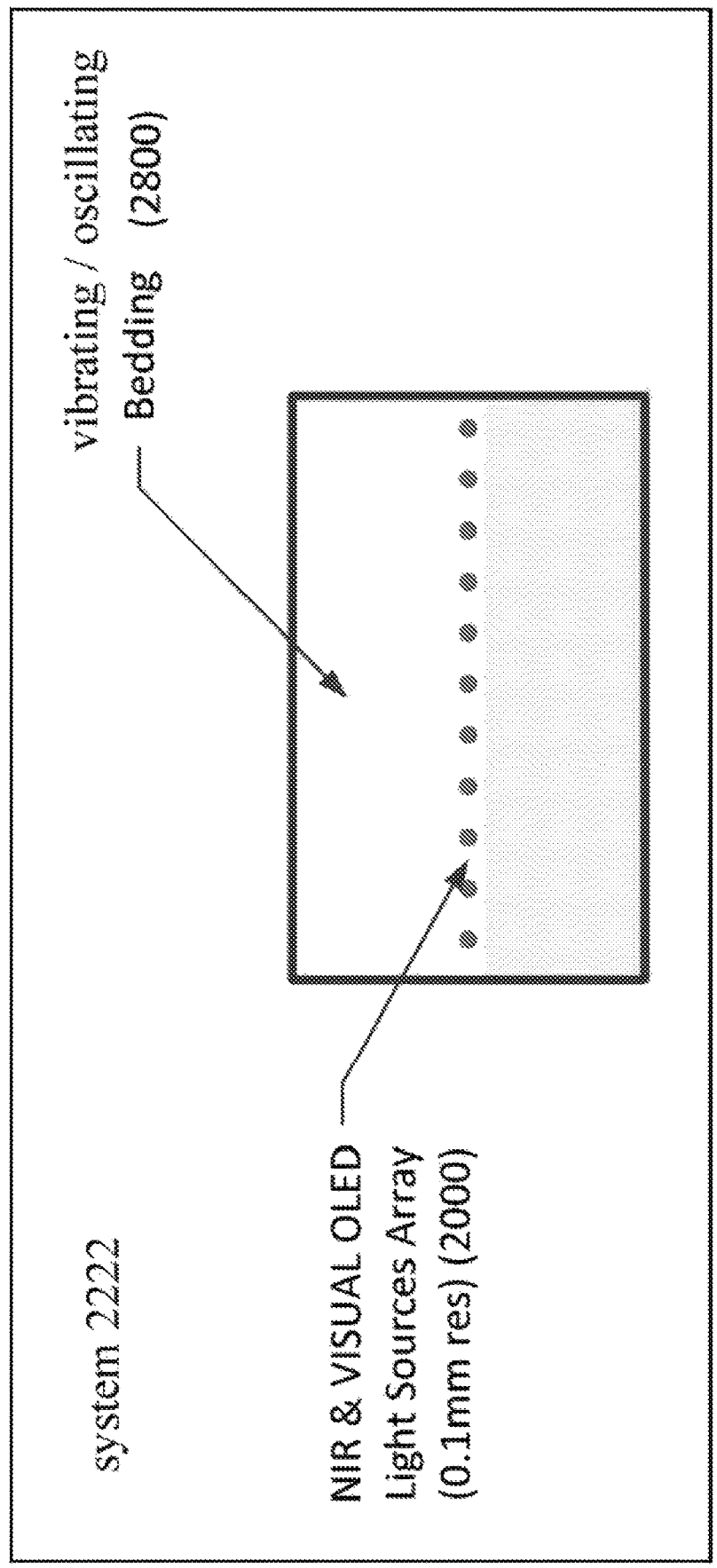
FIG. 2 is a schematic illustration of a vibrating/oscillating illumination system, in accordance with some demonstrative embodiments of the present invention.

Reference is made to FIG. 2, which is a schematic illustration of a vibrating/oscillating illumination system 2222, in accordance with some demonstrative embodiments of the present invention. For example, the set of illumination sources 2000 is connected to, or rests on, or is mounted on, a vibrating/oscillating bedding 2800 or other suitable structure or unit able to vibrate or oscillate based on a pre-defined pattern or schedule. For example, a Micro-Electro-Mechanical Systems (MEMS) unit (or, a vibrating motor or engine or unit; or an oscillating unit) able to vibrate or oscillate may provide the desired vibration or oscillation to the illumination sources 2000 that are mounted on it, or that are connected to it.

The vibration or oscillation of the illumination sources 2000, may be performed along a linear axis; or may be along a two-dimensional area (e.g., along the X axis and also the Y axis; or along the X axis and also the Z axis; or along the Y axis and also the Z axis); or may be along three-dimensional space (e.g., along X axis and Y axis and Z axis); or may be according to pre-defined shape or pattern (e.g., circular back-and-forth movement or rotation).

Accordingly, the spatial location of the illumination source, relative to the human eye, is changing over time, thereby changing also the light output that is reflected back from eye-components towards the sensors 1000; thereby triggering the sensors 1000 to sense changes in light output, which in turn are processed by the processing unit to determine desired parameters. The calculations take into account, in addition to the previously-mentioned data (e.g., the relative location of the illumination units 2000 and the sensors 1000) also known data about the vibration/oscillation of the illumination units 2000, for example, the current real-time status of the oscillating/vibrating operation, in absolute terms or relative to an initial position or initial location or an initial "at rest" position or idle position.

Optionally, the vibrating/oscillating of the illumination sources, in combination with the selective activation and de-activation of particular illumination sources, enables a faster sampling rate and/or a greater sampling resolution; or enables to achieve a desired sampling resolution by utilizing a smaller number of illumination sources.

Figure 3:
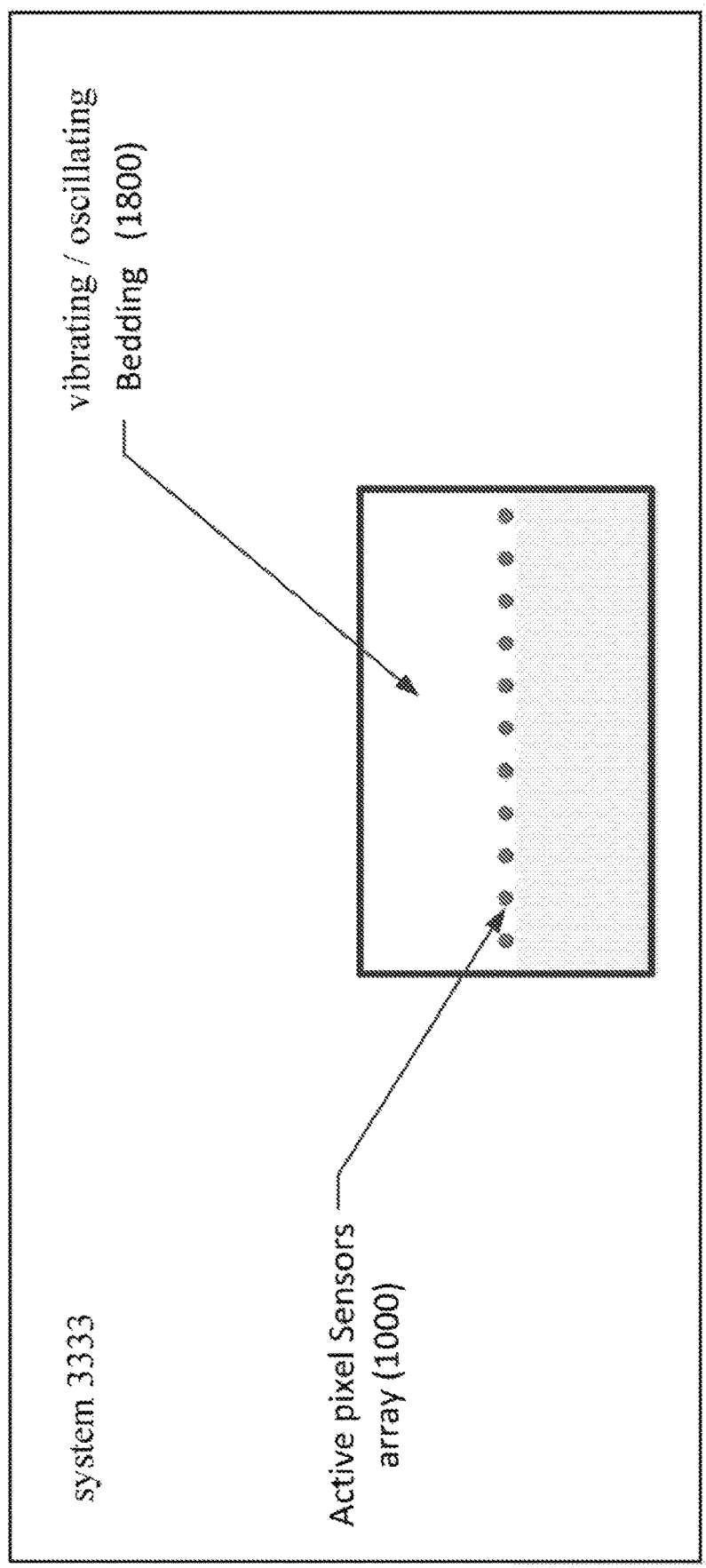
FIG. 3 is a schematic illustration of a vibrating/oscillating sensors system, in accordance with some demonstrative embodiments of the present invention.

Reference is made to FIG. 3, which is a schematic illustration of a vibrating/oscillating sensors system 3333, in accordance with some demonstrative embodiments of the present invention. For example, the set of active pixel sensors 1000 is connected to, or rests on, or is mounted on, a vibrating/oscillating bedding 1800 or other suitable structure or unit able to vibrate or oscillate based on a pre-defined pattern or schedule. For example, a Micro-Electro-Mechanical Systems (MEMS) unit (or, a vibrating motor or engine or unit; or an oscillating unit) able to vibrate or oscillate may provide the desired vibration or oscillation to the active pixel sensors 1000 that are mounted on it, or that are connected to it.

The vibration or oscillation of the active pixel sensors 1000, may be performed along a linear axis; or may be along a two-dimensional area (e.g., along the X axis and also the Y axis; or along the X axis and also the Z axis; or along the Y axis and also the Z axis); or may be along three-dimensional space (e.g., along X axis and Y axis and Z axis); or may be according to pre-defined shape or pattern (e.g., circular back-and-forth movement or rotation).

Accordingly, the spatial location of the sensors, relative to the human eye, is changing over time, thereby changing also the capturing or the detection of light output that is reflected back from eye-components towards the sensors 1000; thereby triggering the sensors 1000 to sense changes in light output, which in turn are processed by the processing unit to determine desired parameters. The calculations take into account, in addition to the previously-mentioned data (e.g., the relative location of the illumination units 2000 and the sensors 1000) also known data about the vibration/oscillation of the active pixel sensors 1000, for example, the current real-time status of the oscillating/vibrating operation, in absolute terms or relative to an initial position or initial location or an initial "at rest" position or idle position.

Optionally, the vibrating/oscillating of the sensors, in combination with the selective activation and de-activation of particular illumination sources, and optionally in combination with pre-programmed oscillation or vibration of the illumination sources, enables a faster sampling rate and/or a greater sampling resolution; or enables to achieve a desired sampling resolution by utilizing a smaller number of active pixel sensors.

Figure 4:
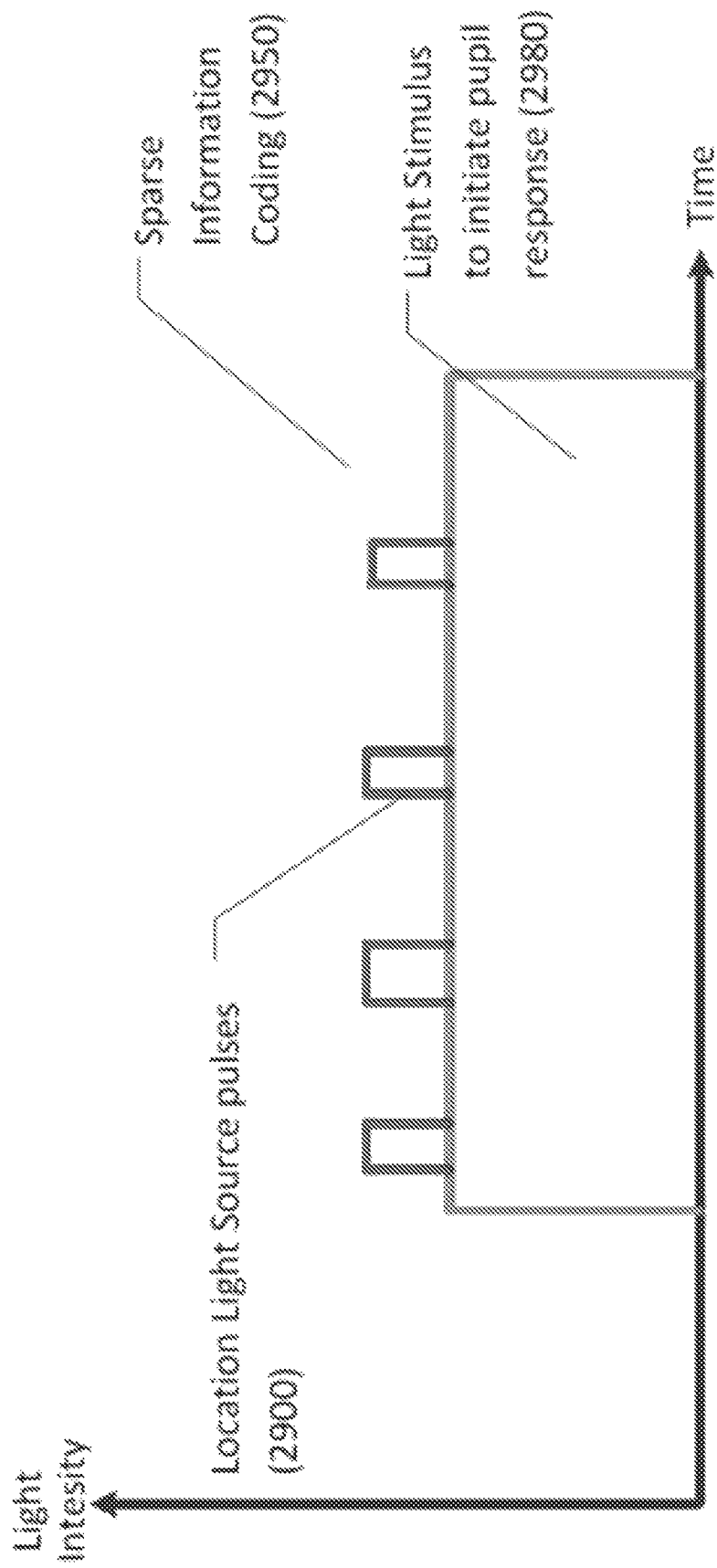
FIG. 4 is a timing/light-intensity diagram of a system, in accordance with some demonstrative embodiments of the present invention.

Reference is made to FIG. 4, which is a timing/light-intensity diagram 4444 of a system, in accordance with some demonstrative embodiments of the present invention. The horizontal axis indicates, or corresponds to, time; whereas the vertical axis indicates, or corresponds to, the intensity of light generated by the set of illumination sources.

As indicated in region 2980 of the diagram, light stimulus is generated by the illumination sources at a generally-constant light-intensity level, in order to trigger or initiate eye-component(s) response (e.g., pupil response, cornea response, blinking, or the like).

As indicated in regions 2900 of the diagram, at particular and spaced-apart time-slots, increased-intensity light-pulses are generated, by one or by some or by all of the illumination sources, in order to trigger a particular, additional (or other) stimulus to the eye or to particular eye-component(s).

In some embodiments, the increased-intensity light-pulses are equally spaced apart, such as, they are fixedly N microseconds from each other; and/or they have a fixed pulse time-length, such as, each light-pulse is activated for M microseconds. In other embodiments, N may be variable and may change among light-pulses; and/or, M may be variable and may change among light-pulses.

For demonstrative purposes, all the four light pulses that are indicated in the diagram, are depicted as having the same "vertical height", such as, having the same value of increased light-intensity. However, in some embodiments, one or more of the light-pulses may have an increased light-intensity that is different from that of one or more other light-pulses. For example, general light-intensity of 50; a first light-pulse having a light intensity of 60; a second light-pulse having a light-intensity of 67; and so forth. In other embodiments, the different light-intensity of one or more of the light-pulses, may even be a lower or a reduced light-intensity, rather than an increased light-intensity; for example, having a reduced light-intensity value of 42 in the above example of values. In some embodiments, one or some of the light-pulses may be increased-intensity light-pulses; and/or, one or some of the light-pulses may be reduced-intensity light-pulses; for example, based on a pre-defined pattern or sequencing scheme, in order to generate a particular pattern of visual stimulus to the eye.

In some embodiments, the time-length of each time-pulse, and particularly of increased light-intensity time pulses, is greater than the minimum time-length or time-resolution of eye changes that the system is able to detect or sense or measure. For example, the sensors may be able to sense a change in eye-component(s) that is at least K microseconds long (e.g., at least 1 or 3 or 4 or 5 or 8 or 10 microseconds); and therefore, the time-length of a time-pulse of increased-intensity (or, reduced intensity) is P microseconds, wherein P is greater than K (for example, P is 12 or 15 or 20 microseconds).

In some embodiments, one or some of the illumination sources, are activated at increased light-intensity level(s), for a pre-defined time-period; thereby causing, for example, response or reaction 2980 by the pupil (e.g., narrowing or shrinking of size-reduction of the pupil) and/or by other eye-component(s). In parallel, the sensing continues by the set of sensors, in a continuous manner (indicated by region 2900), through-out the time-period(s) that correspond to those of the high-intensity light-pulses. The time-length of each light-pulse, relative to time-period that it takes each sensor to sense or detect pixel-level changes, enable the sensor to adjust (immediately, or gradually) to the intensity of the light-pulse(s); and thus the changes (even if visible light is utilized for illumination, and certainly if IR or NIR light is utilized for illumination) are detected or sensed by the sensor(s).

In some embodiments, the time-periods between adjacent light-pulses, are intentionally modified to be non-fixed and non-constant, thereby providing a non-fixed time-interval among light-pulses; as this may increase the Signal to Noise Ratio (SNR) of the sensed data, and/or may reduce or eliminate a situation in which one or more sensors "lock in" on a particular type of change even though it did not actually occur repeatedly.

The Applicants have realized that capturing of full frames or images, at fixed time-intervals, even at a frame-capture rate of 200 (or even 500) frames per second, particularly in a non-controlled environment (e.g., not in a controlled laboratory, but in a "real life" situation such as in a traveling car, in an environment that is moving or shaking or vibrating, in an environment that includes or that is affected by random or non-predicted noises or light flashes), is insufficient for capturing at least some of the ocular movements or ocular characteristics that are able to occur (e.g., to start and to finish) within a time-length that is smaller than the finest time-resolution of such frame-based systems.

The present invention enables efficient, reliable, rapid, accurate, and/or high-quality tracking of eye movements other characteristics of eye components or ocular components; and enables to utilize such information for a variety of purposes, for example, for navigation or driving purposes, for purposes of operating a vehicle or an airplane or a vessel, for purposes of operating heavy machinery (tractor, bulldozer, crane) and/or dangerous machines (gun, rifle, machine gun, tank, cannon, missile), for medical purposes, for diagnosis and/or treatment of medical conditions and/or of physiological conditions (e.g., mental stress, mental fatigue, physical stress, physical fatigue, anxiety, restlessness, fatigue, tiredness, exhaustion), for purposes of determining whether a person is concentrated or focused or alert relative to a particular task or mission, for determining or tracking the gaze or the look or the field-of-view of a user (e.g., a user of an electronic device, smartphone, tablet, laptop, computer, smart-watch, gaming device, Augment Reality (AR) gear, Virtual Reality (VR) gear, or the like), for tracking the eye movements of a student or an online student or an offline student (e.g., particularly while taking an examination or performing a graded assignment, such as, as part of an automated or semi-automated Proctoring system or Auditing system), for entertainment purposes (e.g., as part of a gaming system or gaming console, in which the user controls a virtual character or a virtual object using his vision or gaze), for advertising or marketing purposes (e.g., to generate a "heat map" indicating which regions or components of an advertisement or a screen is actually viewed by the user), for purposes of decision-making or as part of a decision-making process (e.g., with regard to the health or interest of a person; or with regard to a condition of a vehicle or vessel or aircraft or machinery; or with regard to a medical decision); for diagnosis and/or treatment of ocular conditions or mental conditions or physiological conditions or neurological conditions; to detect or estimate a mood or state-of-mind of a person, or to detect or estimate anxiety, lack of anxiety, existence of anxiety, level of anxiety, level of alertness; as part of cognitive and/or behavioral analysis or decision-making process, or environmental decision-making process; as part of an Augmentative Alternative Communication (AAC) device or system; as part of a system that utilizes eye-movement for communication purposes (e.g., by a paralyzed or disabled person, or by a person having a locked in syndrome (LIS) or pseudo-coma); for military purposes; for security purposes; for medical purposes as part of an endoscopic system or an endoscope or stent or catheter or guide-wire or a swallowable imaging capsule or a swallowable camera); for purposes of athletic training; to detect saccade, pupil dilation, ocular problems, ocular abnormality, abnormal behavior of ocular component(s), blinks, fixations, or the like; as part of, or integrated within or mounted on, a helmet or head-gear or a wearable device (e.g., AR gear or VR gear); as part of a fighter-pilot helmet, or a civil aviation gear or system; as part of a motorcycle helmet; as part of a vehicular dashboard, or as part of a vehicle or vessel or aircraft (e.g., the system being directed towards the estimated location of the head of the driver/pilot/operator); for in-flight or in-drive health monitoring; to detect ocular swelling (e.g., due to a change in air pressure or other causes); and/or for other suitable purposes.

Figure 5:
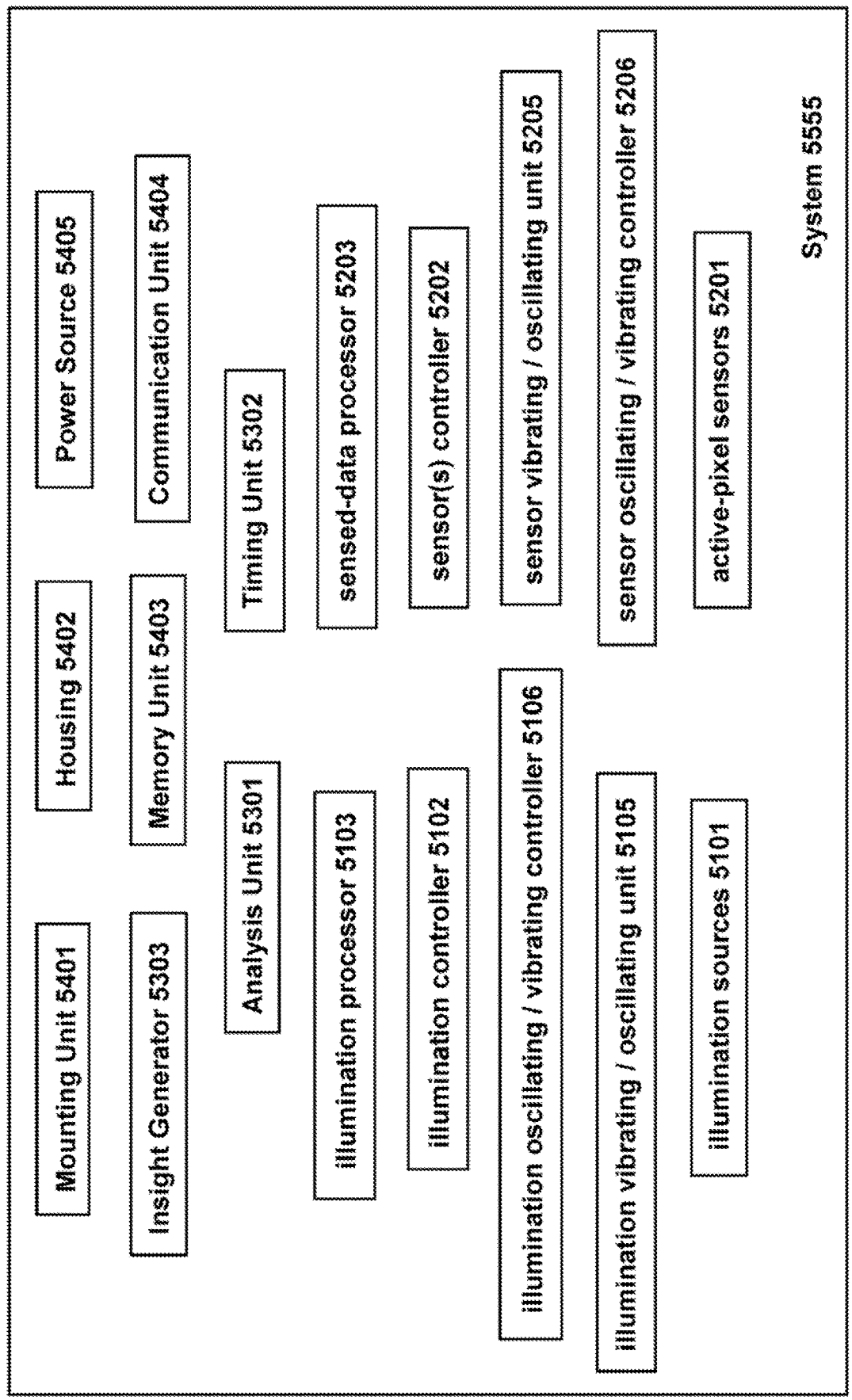
FIG. 5 is a schematic block-diagram illustration of a system, in accordance with some demonstrative embodiments of the present invention.

Reference is made to FIG. 5, which is a schematic block-diagram illustration of a system 5555, in accordance with some demonstrative embodiments of the present invention. For example, system 5555 may be or may comprise one or more of the components that were described above; and/or may perform one or more of the methods or operations described above; or, one or more of the components or systems that were described above may be implemented as system 5555, or may comprise system 5555 and/or one or more of its components.

For example, a set of illumination sources 5101 able to selectively generate illumination, as regulated or controlled by an illumination controller 5102. A set of active-pixel sensors 5201, controlled by a sensor(s) controller 5202, is able to sense or detect pixel-based or pixel-level changes, within an area-of-interest that is illuminated by one or more of the illumination sources 5101.

Optionally, an illumination processor 5103 may process data or may process a pre-programmed code that enables illumination in accordance with a pre-defined pattern or scheme. A sensed-data processor 5203 may process signals or data outputted by the sensors 5201, for example, signals received from such sensors in non-synchronous manner, at random or pseudo-random time intervals, at non-predictable time-intervals or time-points.

An analysis unit 5301, optionally coupled to a timing unit 5302 (e.g., utilizing a Real Time Clock (RTC) or other timer), may analyze data, and particularly may analyzed fusion of data that indicates the particular illumination that was activated (and its timing) with the particular reactions or responses that were sensed or detected. Optionally, a lookup table or a set of threshold values or ranges-of-values, may be used by an Insight Generator 5303 to generate one or more insights with regard to the user whose eye is being monitored or tracked.

Optionally, an illumination vibrating/oscillating unit 5105 operates to vibrate, oscillate, or otherwise move or shake the illumination source(s) or some of them; controlled by an illumination oscillating/vibrating controller 5106.

Optionally, a sensor vibrating/oscillating unit 5205 operates to vibrate, oscillate, or otherwise move or shake the active-pixel sensors or some of them; controlled by a sensor oscillating/vibrating controller 5206.

Optionally, components of system 5555 may be coupled or connected to, for example, a mounting unit 5401 which may be part of, or connected to or mounted to, another device or system; for example, a helmet, a dashboard, a vehicular dashboard, an aircraft dashboard, a gaming console or gamine device, an AR gear or device, a VR gear or device, a medical device or medical system or imaging system, a safety/security system or device, a military device, a civil device, or the like.

Optionally, some or all of the components of system 5555 may be housed in, or ay encapsulated within, or may otherwise be integrated in or with, a housing 5402 or other suitable structure; for example, a helmet, sunglasses, AR gear, VR gear, a dashboard, a vehicular dashboard, an aircraft dashboard, a medical device, a computer, an electronic device, a smartphone, a tablet, a gaming console or gaming device, a smart-watch, and/or other suitable structure of device.

System 5555 may further comprise other suitable units and/or modules; for example, a memory unit 5403 to store sensed data and/or processed data; a communication unit 5404 (e.g., wireless transceiver, Wi-Fi transceiver, Bluetooth transceiver, cellular transceiver, wire, cable) to transfer data to a remote recipient and/or receive data from remote sources over wireless link(s) and/or wired link(s); a power source 5405 (e.g., battery, rechargeable battery, connection to electric socket) to provide power to other components; and/or other suitable units.

One or more of the devices or systems of the present invention, may optionally comprise one or more other types of sensors, and/or may be implemented to operate in association with one or more other types of sensors. For example, the devices and systems of the present invention, may receive additional information and/or augmented data that is sensed or measured by other sensors, and/or that is obtained by other units or processors. Additionally or alternatively, the devise and systems of the present invention, may operate as an information source for other systems, and/or for co-located systems or nearby units. Such other systems may be, for example, an Electroncephalography (EEG) system or unit, an Electrooculography (EOG) system or unit, a Functional NIR Spectroscopy (FNIRS) system or unit or imager, a pletismograph system or unit, a Magnetic Resonance Imaging (MRI) system or unit, a Computed Tomography (CT) scanner, an ultrasound imaging system, a polygraph machine or unit, and/or other systems, units and/or sensors; thereby enabling a processor to perform decision-making processes or determination processes that are based on fusion of data from multiple types of sensors and/or from multiple sources of information.

Figure 6:
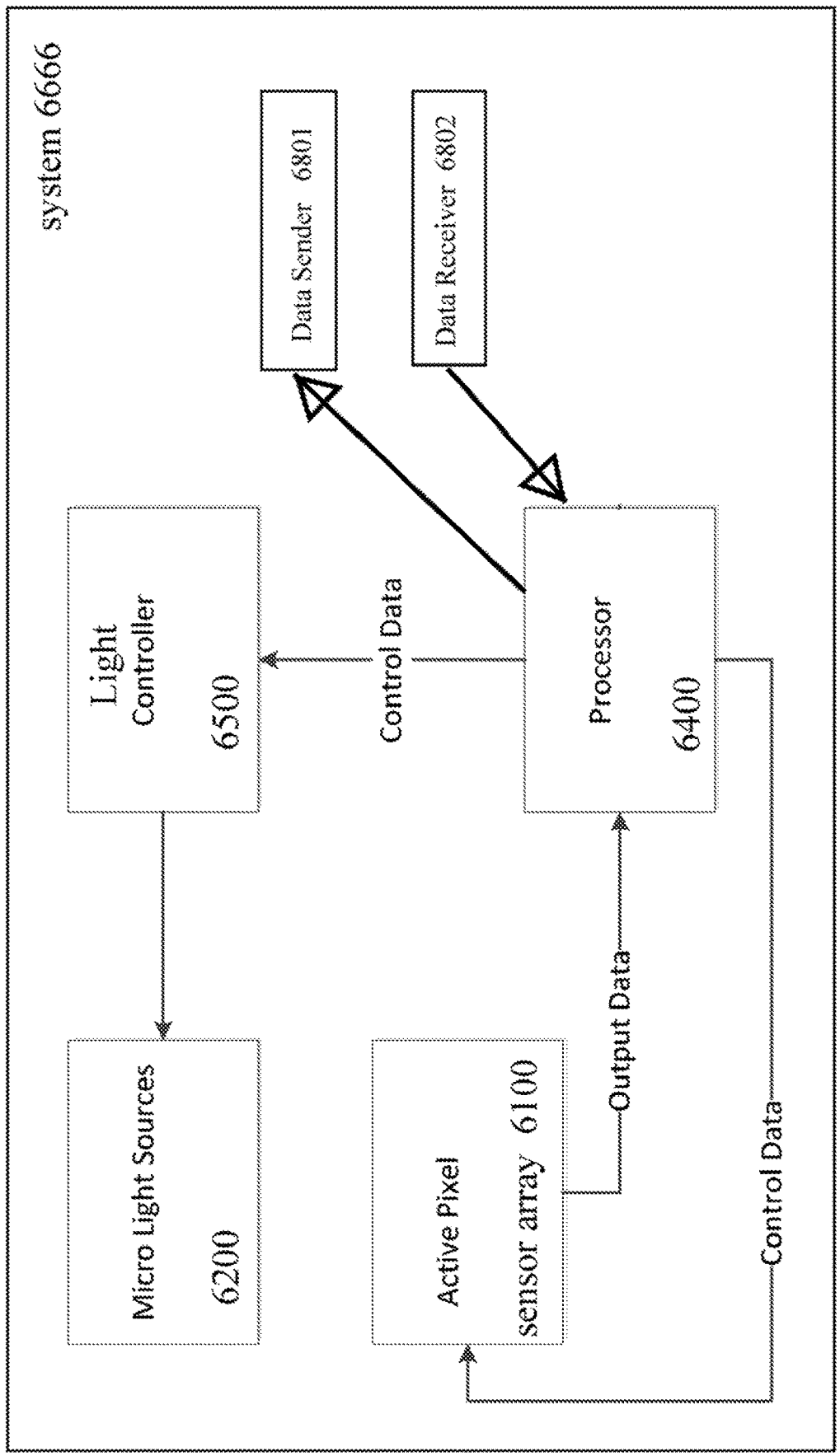
FIG. 6 is a schematic illustration of a system, in accordance with some demonstrative embodiments of the present invention

Reference is made to FIG. 6, which is a schematic illustration of a system 6666 in accordance with some demonstrative embodiments of the present invention. System 6666 comprises a set of illumination sources, such as micro light sources 6200; and a set of optical sensors or detectors, such as active pixel sensors array 6100. A processor 6400 transfers control data to a light controller 6500, which controls and/or modifies the operations of the micro light sources 6200 or the set of illumination sources. The optical sensors, such as the active pixel sensors array 6100, transfer their output data or output signals to the processor 6400.

Processor 6400 processes the output data and/or the signals, that were received from the active pixel sensors array 6100; optionally while also taking into account the data received via a data receiver unit 6802 from one or more other sensors, detectors, imagers and/or measuring units. Additionally or alternatively, the data that was processed by processor 6400, based on the signals from the active pixel sensor array 6100, and optionally fusing also data from such other sensors detectors, imagers and/or measuring units, may be further transferred via a data sender unit 6801 to one or more remote or co-located units or systems, in raw format and/or in processed format.

Some embodiments of the present invention may operate to sense and/or measure properties of a region or area-of-interest, in a closed environment or a closed chamber or a closed system; for example, as part of an endoscope or an in-vivo sensing device able to sense properties within a human body; such as, as part of (or in conjunction with) surgery, treatment, diagnosis, medical procedure, medical measurement, medical imaging medical sensing, and/or other operations. The sensitivity of the active pixel sensors, and the utilization of rapid illumination units, enable the system to remotely sense an area-of-interest, without necessarily requiring to move the sensors and/or the illumination units to be proximate to the area-of-interest. Such remote sensing, in accordance with the present invention, reduces or eliminates the difficulty to approach a particular area-of-interest (e.g., which may be difficult to approach, or which may be small or narrow), and/or reduces or eliminates the heating of such area-of-interest due to illumination units, and/or does not suffer from other problems that imagers or cameras may have (e.g., difficulty to focus on a target when located in proximity to the target; difficulty narrow dynamic range of the image captured by a camera in such situation; reduced quality of the image due to shaking or vibrating of the hand of the operator of the camera; low contrast of the image captured by a camera which in turn makes it difficult or impossible to distinguish among objects which may otherwise be sensed via NIR light with the system of present invention, such as tumors or inflammations).

Figure 7:
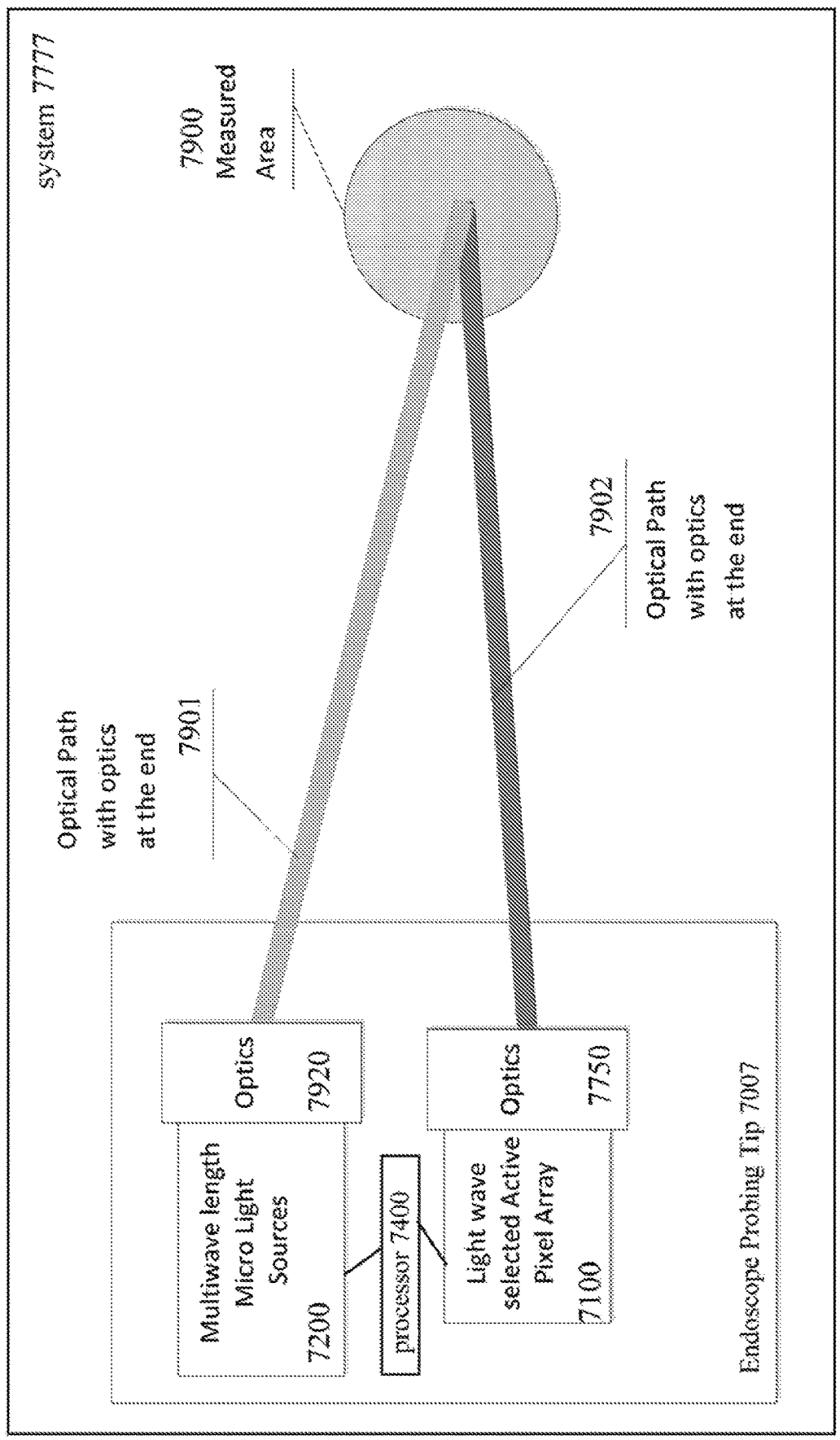
FIG. 7 is a schematic illustration of an endoscopic system, in accordance with some embodiments of the present invention.

Reference is made to FIG. 7, which is a schematic illustration of an endoscopic system 7777, in accordance with some embodiments of the present invention. System 7777 may comprise an endoscope probing tip 7007, which includes a set of multi-wavelength micro light sources 7200, or a set of illumination sources having different wavelengths; which generates light that passes through optics elements 7920. The light progresses along a first (outgoing) optical path 7901 which is directed towards an area-of-interest or an object-of-interest, located in a measured area 7900; some of the light (and not necessarily all of the light) is reflected from that area or object, along a second (incoming) optical path 7902, towards optics elements 7750 and from them to a set of active pixel sensor array 7100, which generate output signals. A processor 7400, which may be local in the endoscope probing tip 7007 or may be remote from it (e.g., located at a different region of the endoscope, and not necessarily in the probing tip) operates to control the operation of the set of illumination units, and/or to process the output signals generated by the set of active pixel sensors.

In some embodiments, the set of illumination units generate light, at different wavelengths, which is modulated at high rate, towards the area-of-interest. In some embodiments, the optics elements 7920 focus the generated light, for example in order to provide more illumination to a particular area-of-interest. In some embodiments, the optics elements 7920 may vibrate or may oscillate (e.g., using a vibrating/oscillating unit); for example, vibrating along the Z axis or the Depth axis, thereby enabling the system, over time, to direct the measurement towards a nearby focal point and/or towards a distal focal point, and/or to sense three-dimensional properties or depth-related properties of the sensed object or the sensed area-of-interest. In some embodiments, by modifying the focal distance of the optics elements, in a controlled and generally continuous manner (or, in discrete intervals that are sufficiently small), a depth-from-focus algorithm or other suitable method may be used to determine or calculate the depth of the object-of-interest or of the area-of-interest, or to otherwise construct a three-dimensional representation of the area-of-interest or object-of-interest. In some embodiments, the optics elements may be fixed, or may be adaptive optics or "liquid lens" optics; for example, to enable successful focusing of the light at the object-of-interest even when the endoscope probing tip is located in proximity to the object. In some embodiments, the system performs rapid sensing at a high rate, which thus enables the system to be less affected (or, not to be affected) by natural vibrations or shaking of the entire system or of the human operator, and further enable to stabilize and correctly sense the features of the area-of-interest or the object-of-interest.

Figure 9:
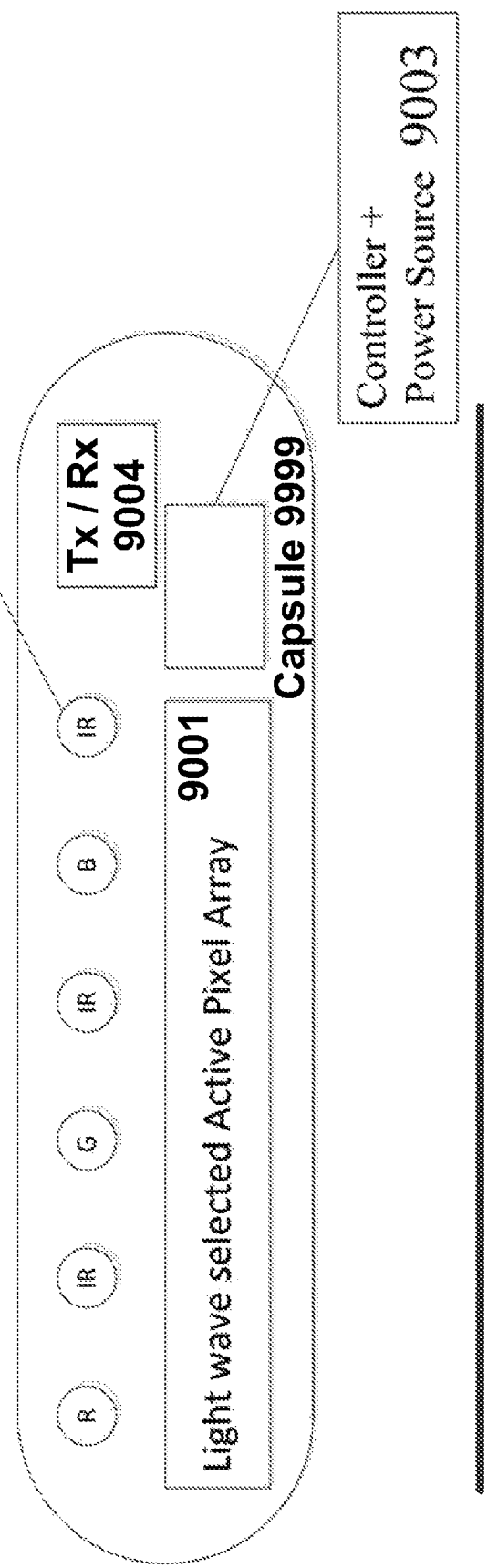
FIG. 9 is a schematic illustration of a medical device, in accordance with some demonstrative embodiments of the invention.

Reference is made to FIG. 9, which is a schematic illustration of a medical device in accordance with some demonstrative embodiments of the invention. The medical device is a capsule 9999, for example, an in vivo capsule, a swallow-able or swallowable capsule, an autonomous capsule, a diagnosis imagine capsule, or other type of capsule that a human user can swallow and which traverses the G.I. tract, collects or captures data in vivo, and wirelessly transmits data (while still in vivo) to an external (ex vivo) wireless receiver device. For demonstrative purposes, capsule 9999 is shown within a body lumen 9100, such as the G.I. tract or the intestine; although other suitable body lumens may be sensed by using a similar autonomous in vivo capsule of the present invention, for example, a blood vessel, a vein, or the like. The in vivo capsule 9999 is autonomous, such that it is not connected to and is not coupled to a guiding wire or a guide-wire or a catheter or a stent or a wire or a cable or other unit; and it is not being manually controlled or navigated by a human operator (e.g., a physician) as it travels in vivo within the patient's body.

The in vivo capsule is inserted into the body lumen 9100; for example, it is swallowed by the patient, or it is injected or inserted into the body lumen via other means (e.g., injector; or other capsule delivery mechanism). Instead of (or in addition to) having a camera or an imager, the in vivo capsule 9999 of the present invention comprises a set of illumination sources 9002 able to generate light pulses (e.g., visible light, or IR light, or NIR light; or a particular pre-programmed scheme of various wavelengths of light; or a combination of the above) at particular time intervals or in accordance with a timing scheme; and a set or array of active pixel sensors 9001 is responsive to pixel-level changes, and such sensors 9001 generate output signal(s) in a non-synchronous manner upon detecting of a change in the relevant pixel being monitored. The illumination sources 9002 and/or their illumination properties are modulated or modified rapidly and/or for short periods of times, and consume low energy. A controller and power source module 9003, such as a controller coupled to a "button" battery, provide power to the illumination sources 9002 and the active pixel sensors 9001 and also control their operation and modify their operational properties. The active pixel sensors 9001 provide a wide dynamic range of sensing; particularly since the controller knows which one(s) of the illumination source(s) 9002 was activated, for how long, and at which wavelength it illuminated. This information, when fused together with the output signals generated by the active pixel sensors 9001, either locally within the capsule 9999 or remotely/externally by an external processing unit, enables the system to detect and/or to identify a condition or an object in or near the body lumen 9100, such as a tumor/inflammation/object (e.g., worm, parasite) 9200.

The raw data that is outputted by the active pixel sensors 9001, and/or such data after it was at least partially processed within the capsule 9999 by the controller 9003 (e g, taking into account the particular data that the controller has about the respective timing of the illumination, the wavelength of illumination, the number and location of the illumination sources that were activated, or the like), are transmitted wirelessly via a transmit/receiver unit (e.g., a wireless transmitter or transceiver, a Wi-Fi transmitter or transceiver, a cellular transmitter or transceiver, a Bluetooth transmitter or transceiver, a Zigbee transmitter or transceiver) towards an external receiver/processing unit (e.g., which may be worn or carried by the patient).

The wirelessly transmitted data is smaller in size (e.g., number of bytes) and/or is shorter in transmission time (e.g., milliseconds), relative to a transmission of full image frames that an in vivo camera captures and transmits. Accordingly, the transmission time is shorter, and the battery life of the power source of the capsule 9999 is longer; or, a smaller battery (e.g., having a small form-factor) may be used in the capsule 9999, thereby making the entire capsule smaller and/or lighter relative to an in vivo camera capsule, and thereby enabling a larger population of patients to swallow such smaller capsule.

The utilization of particular illumination sources 9001, particularly in the NIR range of the spectrum, enables the capsule 9999 to obtain responses from tumors, inflammations, objects (parasite, worm) and/or other items of interest (e.g., blood clot, bleeding region, feces), and may enable the system of the present invention to characterize such items or objects (e.g., their size, dimensions, locations, temperature, shape) relative to (and distinguished from) the body lumen 9100 or their surroundings.

Figure 8:
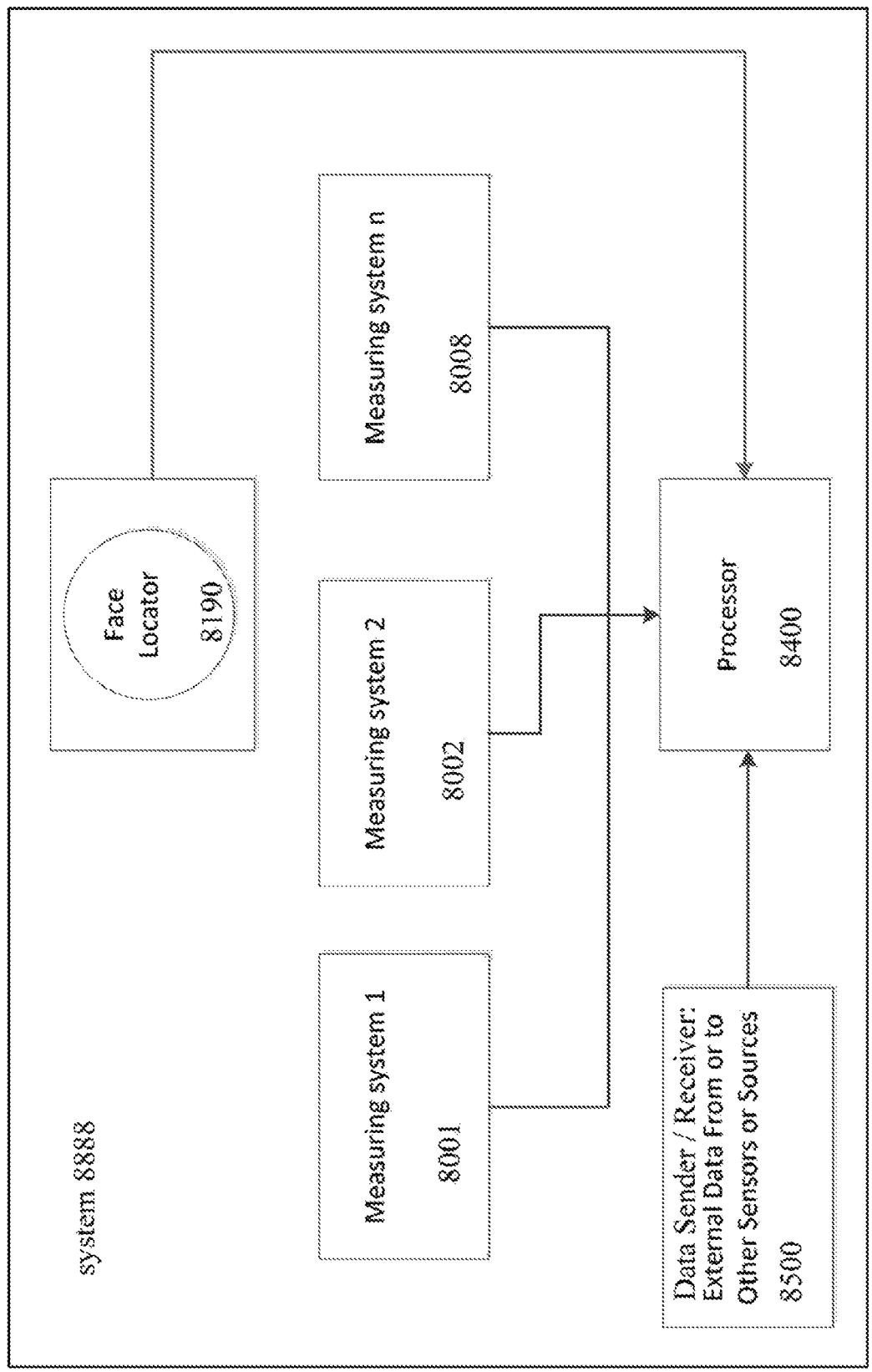
FIG. 8 is a schematic illustration of a multi-sensor system, in accordance with some demonstrative embodiments of the present invention.

Reference is made to FIG. 8, which is a schematic illustration of a multi-sensor system 8888, in accordance with some demonstrative embodiments of the present invention. System 8888 may be configured to operate efficiently in an environment or location in which the human user has a wide field for movement, such as a cockpit of an aircraft in which a pilot may move his head towards various instruments or regions. In such environment, it may be difficult to obtain reliable results from a single sensing device; and therefore, multiple sensors or multiple sub-systems of sensing are utilized (e.g., measurement system 8001; measurement system 8002; and so forth, indicated by measurement system 8008). The multiple sensing units or sensors or sensing sub-systems are managed, controlled, activated and de-activated in a selective manner, by a processor 8400. Optionally, a data sender/receiver unit 8500 is used by the processor 8400, for receiving additional information from external sources or other sources (e.g., to receive flight-related or aircraft-related information, such as current altitude, current air speed, or the like), and/or for sending processed data (and/or raw data) to other systems or units or recipients.

In some embodiments, process 8400 selectively activates and de-activates one or more, or some, of the various sensors or measurement systems (8001, 8002, 8008); for example, based on an analysis that estimates which sensor(s) are currently in the field-of-view of the pilot and thus enable to capture useful readings, or in contrast, which sensors are currently away from the field-of-view of the pilot and thus are not expected to provide useful readings. In some embodiments, a face locator unit 8190 may be used, for example, implemented using a camera or imager or thermal camera or thermal imager, and/or by using computerized vision; the face locator unit 8190 detects the location and/or direction and/or orientation of the face (or the head) of the human subject. For example, a thermal camera may be used for this purpose, utilizing a temperature-based mask or template which distinguishes between a generally-cold cockpit environment and a generally-hot human face of facial-area. Accordingly, such face locator unit 8190 may operate with little or more computational requirements of its own, and may provide useful insights to the processor 8400 in order to selectively and timely activate and/or de-activate one or more, or some, of the various sensors or measurement sub-systems.

Some embodiments of the present invention utilize only non-dangerous or non-harmful light or illumination or units; for example, components that are pre-approved or pre-tested to be safe for utilization in proximity to (or being directed towards) a human eye, and/or components that generate light or electromagnetic radiation at a particular wavelength and/or frequency and/or intensity that is determined to be safe or non-harmful to humans (e.g., based on measurements, by using a focus group of human testers, based on medical research, or other sources). In some embodiments, non-laser light is generated and/or utilized.

Some embodiments of the invention have utility and may assist a user or a system, even if such embodiments do not necessarily operate 100 percent of the time or continuously. For example, a vehicular dashboard, or a dashboard of an aircraft, may comprise a system in accordance with the present invention, being directed generally towards the location of a head of a driver or pilot or operator (e.g., being fixedly directed towards the upper-region of a seat of such pilot or driver or operator). The user (e.g., pilot, driver, operator) may be located there, but may sometimes move his head to be away from the field-of-view of the system of the present invention (e.g., the user bends-down to push a button, or stretches sideways to reach a lever, or the like), or the user may sometimes turn his head sideways (e.g., 90 degrees to the right, or to the left). In such time-periods, the system of the present invention may not be able—temporarily—to generate light beams that reach or "hit" the eye of the user; and thus, the system may not be able to detect or sense ocular data during such time periods. However, the system of the present invention may still have utility and may assist the user (or may assist an inter-connected system, such as the vehicle or aircraft itself), at least during the time-periods (even if they are short and/or spaced-apart) in which the light generated by the system does reach or does "hit" the eye of the user and is reflected from it towards the sensors of the present invention. Accordingly, even if during (for example) 30 seconds of operating an aircraft, the pilot's eye is located for one second within the specific field-of-view of the illumination units and sensors of the present invention (e.g., 1 out of 30 seconds, or 3.33 percent of the time), this may still be sufficient in order to obtain a desired sampling of the pilot's eye, and may still be sufficient in order to generate useful insight(s) with regard to the pilot's condition (e.g., fatigue, stress, pressure, reduced vision, abnormal ocular condition, medical condition, mental condition, or the like). Accordingly, even if the system of the present invention is effectively operational during a small portion of a timeline, it may still generate helpful insights and still has utility. Additionally or alternatively, in some embodiments, the percentage of time in which the system is effectively operational, may be increased by implementing the system as an integrated part of, or integral part or, or as being mounted on, a helmet or head-gear or wearable item which is constantly or almost-constantly located around or in proximity to a human eye and/or does not change its own location or position relative to the human eye.

Some embodiments of the present invention may acquire and capture or sense information, or may cause or trigger the generation of unique information, by actively and selectively performing particular modification(s) of the illumination sources or of some of them, and particularly by modifying one or more operational properties of some (or all) of the illumination sources which are responsive to (or, which sense only or exclusively) changes in the object-of-interest (e.g., the eye, or a particular portion or region of the eye); rather than by directly modifying the object-of-interest and/or its immediate environment. In some embodiments, the sensors or imagers of the system of the present invention, are responsive only to (or, exclusively to) changes in the imaged or sensed object-of-interest or area-of-interest, rather than being generally responsive to (or, generally capturing data from) the object-of-interest regardless of whether or not it had changed one or more of its properties.

These features enable the system of the present invention to generate and to sense a new type of information from the object-of-interest, and particularly from the eye or from a portion or area of the eye, in response to selective and pre-defined modifications of operational properties of some or all of the illuminating units and/or sensors that are used. Additionally or alternatively, these features enable the system of the present invention to operate rapidly and to generate and obtain results rapidly, and/or to receive or fetch or obtain responses from several sensors or from few sensors (or conversely, from numerous sensors, if desired in some implementations) whose spatial location relative to the illumination source(s) is known or is pre-defined, thereby enabling an immediate or real-time or near-real-time spatial sensing process.

In some embodiments, the system of the present invention may optionally perform and/or utilize selective and/or patterned and/or timed vibration and/or oscillation of the illumination sources or their bedding or their mounting platform or their structure (e.g., as demonstrated in FIG. 2 and/or FIG. 3), instead of or in addition to the modulation and/or the modification of other properties of the illumination sources (e.g., the selective activation or de-activation of some particular illumination sources; the modification of the wavelength of one or more some or all of the illumination sources; the modification of the angular position or directional aiming of one or more of the illumination sources; or the like), in order to trigger the generation and/or the sensing of unique or additional information about the object-of-interest, and/or in order to modify or increase the frequency or the effective rate of data collection or data sensing.

In some embodiments, the system may sense and/or capture data only in response to particular or selective modifications that are caused, or may be responsive only to the result(s) of such caused modifications, rather than continuously capturing or continually acquiring data (e.g., as a continuum stream of captured data, or at pre-defined or fixed time intervals); thereby reducing significantly the volume or the size of the data that is actually captured and/or sensed and/or processed and/or stored; and/or thereby enabling the system of the present invention to utilize an increased effective rate or frequency of sensing or capturing data, and/or thereby enabling the system to reach an effective sampling rate that may even be an order of magnitude or multiple orders of magnitude greater than conventional devices.

The present invention provides an innovative solution which may provide unique benefits and features. Indeed, a conventional illumination unit may be modulated at a high frequency or at a high rate; however, the resolution of the captured data would still be the resolution of the sensor involved, and a high-resolution sensor would generate an immense size of captured data which requires significant storage resources and/or significant processing resources and/or which cannot be efficiently or effectively processed in real-time or in near-real-time and/or that cannot be efficiently or effectively transferred or transmitted to other locations (e.g., processing locations, storage locations, or other recipients), and/or that cannot be effectively or efficiently performed in a device having a small form-factor or small foot-print or a relatively modest processing power or a relatively small storage capacity; and which would require expensive and/or time-consuming and/or processing-intensive spatial analysis or spatial processing or spatial separation or spatial differentiation.

In contrast, the system of the present invention may achieve or may utilize an effective resolution which is a function of (or, which depends on) the resolution of an array or matrix or set of sensors, such as a set of LED or OLED sensors and/or a MEMS component and/or a MEMS-based or LEDs-based scanning mirror or scanning component; which utilizes or senses or acquires (or is responsive to) the modifications in reflected light that was illuminated (e.g., selectively) from one or more particular illumination sources, using (e.g., selectively) one or more illumination wavelengths, and by taking into account the known or pre-defined spatial position or spatial location of the illumination source(s) relative to the sensors and/or relative to the object-of-interest. Accordingly, in some embodiments of the present invention, the system may utilize sensors having reduced resolution (which, in turn, may translate into less-expensive sensors; and/or which, in turn, may translate into a reduction in processing resources, reduction in storage resources, reduction in processing time, reduction in transmission time to other recipients, and/or enablement of real-time processing or near-real-time processing); and/or which may enable the utilization of less-accurate or less-expensive spatial analysis or spatial differentiation or spatial (since, for example, a single scanning relative to a pre-defined target may be utilized for initial calibration or re-calibration of the system).

Some embodiments of the present invention do not utilize an assumption that the illumination source generates an illumination beam that causes a single-point or a single-pixel to respond and/or that causes a reflection that only a single sensor or a particular sensor would then sense or acquire. Rather, some embodiments of the present invention may operate based on an operational premise that several different sensors would sense the reflected light of a single illumination source (or, of multiple illumination sources that are operated selectively). Furthermore, since the system may utilize reduced-resolution sensors, the number of sensors that would actually react and sense data in response to the selective modifications of illumination, would be a relatively small number (e.g., 2 or 3 or 4 or 6 or 8 sensors, in some embodiments), which in turn may enable the system to efficiently and/or accurately determine or calculate or find the central point that corresponds to them and which is the actual point of impact (e.g., by calculating the center of gravity of the signal strength of the received signals as sensed across the multiple sensors, and/or by determining or calculating a spatial average or a spatial weighted-average of the data sensed by the N sensors having the highest signal strength; wherein N is, for example, 2 or 3 or 4 or other suitable value).

Some embodiments may further enable an effective increase in the field-of-view that is covered by the illumination and sensing system of the present invention, particularly by chaining multiple modifications or modulations across multiple parameters or variables; for example, by selectively moving or oscillating or vibrating the illumination source (or some of them) and/or the sensors (or some of them), and/or by modifying the time-domain features of such units (e.g., the time-slots or time-periods in which particular illumination sources are activated or de-activated, or the time-intervals between such activation/de-activation operations), and/or by selectively modifying the wavelength(s) of the illuminated light from some or all of the illumination sources based on a pre-defined pattern or scheme, and/or by modifying the angular position or the angular direction or the spatial location(s) of one or more of the units of the system (e.g., the illumination sources and/or the sensors) while still utilizing their current and known spatial position or location as a parameter that is taken into account in order to calculate the results). The aggregation of these modifications, in two or more domains or in multiple types of parameters, may thus enable the system to achieve an increase in the accuracy of the sensed results and/or the processed results and/or the effective field-of-view that is covered or monitored or processed by the system.

For demonstrative purposes, some portions of the discussion may relate to LED or OLED or LED-based or OLED-based illumination sources; however, these are only non-limiting examples; and in some embodiments, the illumination sources may include, for example, laser or laser-based illumination sources, laser generator, laser transmitter, Laser Diode (LD), diode laser, diode-based laser, injection laser diode (ILD), semiconductor laser unit, optically pumped semiconductor laser (OPSL), double hetero-structure laser, quantum well laser, Distributed Bragg Reflector (DBR) laser, Vertical-Cavity Surface-Emitting Laser (VCSEL), visible light laser units, infrared laser units, or other suitable units able to generate laser beams or laser illumination, and/or able to modulate such laser beam(s) and/or transmissions, and/or able to selectively modify the wavelength of such laser beam(s) and/or transmissions, and/or able to selectively activate and de-activate such laser units, and/or able to selectively generate laser or laser-based pulses or illumination, or the like. In some embodiments, the optical sensors or optical detectors may be configured or adapted to particularly sense or detect, or to be responsive to, changes in the reflection or the feedback of the illuminated laser beam(s).

Some embodiments may utilize only illumination sources (e.g., LED or OLED or laser based) that are deemed to be "safe" for human usage, or that generate beams or radiation or light that are deemed to be "safe" for human usage; for example, laser beam(s) or source(s) that are known to be non-damaging to human body and/or to human eyes, or laser beam(s) or source(s) that are known to be non-damaging even if hitting human eyes for a short period of time. Some embodiments may utilize, for example, Eye-Safe laser, infra-red laser, infra-red optical signal(s), low-power laser or low-strength laser, and/or other suitable type(s) of optical signals, optical beam(s), laser beam(s), infra-red beam(s), or the like. It would be appreciated by persons of ordinary skill in the art, that one or more suitable types of laser beam(s) or laser source(s) may be selected and utilized, in order to safely and efficiently implement the system and method of the present invention. In some embodiments, optionally, a human user may be requested to wear sunglasses or protective eye-gear or protective goggles, in order to provide additional safety to the eyes of the human user which may occasionally be "hit" by such generally-safe laser beam, as an additional precaution.

In some embodiments, a system comprises: a set of illumination sources, to selectively generate illumination pulses towards a human eye in accordance with a particular timing scheme per illumination source and in accordance with a particular wavelength per illumination source; a set of optical sensors, to sense changes to one or more properties of reflections of said illumination pulses (or, of reflected optical feedback that is reflected back) from the human eye in response to modifications in operational properties of said set of illumination sources; a processor to process the sensed changes, and to generate one or more processing results that are based on said sensed changes.

In some embodiments, said optical sensors are configured to exclusively sense and to be responsive only to changes in reflections from an object within the field-of-view of the optical sensors.

In some embodiments, the processor generates said processing results by taking into account also (i) known spatial distances between the illumination sources and said human eye, and (ii) known spatial distances between the optical sensors and said human eye.

In some embodiments, the system comprises: an oscillation controller to cause selective spatial oscillation of said illumination sources; wherein the processor generates said processing results by taking into account said selective spatial oscillation of said illumination sources.

In some embodiments, the system comprises: a vibration controller to cause selective spatial vibration of said illumination sources; wherein the processor generates said processing results by taking into account said selective spatial vibration of said illumination sources.

In some embodiments, the system comprises: a motion controller to cause selective spatial motion of said illumination sources; wherein the processor generates said processing results by taking into account said selective spatial motion of said illumination sources.

In some embodiments, the system comprises: a wavelength modification controller, to cause selective modification of wavelength of only some but not all of said illumination sources; wherein the processor generates said processing results by taking into account said selective modification of wavelength of only some but not all of said illumination sources.

In some embodiments, the system comprises: a wavelength modification controller, (i) to cause a first illumination source and a second illumination source to illuminate at a same particular wavelength, and (ii) to cause selective modification of the wavelength of illumination of the first illumination source while maintaining the wavelength of illumination of the second illumination source; wherein the processor generates said processing results by taking into account said selective modification of wavelength.

In some embodiments, the system comprises: a wavelength modification controller, (i) to cause a first illumination source to illuminate at a first wavelength, and (ii) to cause a second illumination source to illuminate at a second wavelength, and (iii) to cause selective modification of the wavelength of illumination of the first illumination source while maintaining the wavelength of illumination of the second illumination source; wherein the processor generates said processing results by taking into account said selective modification of wavelength.

In some embodiments, the system comprises: a wavelength modification controller, to cause modification of wavelength of all of said illumination sources in accordance with a particular timing scheme; wherein the processor generates said processing results by taking into account said selective modification of wavelength of and said particular timing scheme.

In some embodiments, said illumination sources comprise LED-based or OLED-based illumination sources that are capable of temporarily modifying their illumination wavelengths based on wavelength modification commands.

In some embodiments, said optical sensors comprise a group of Active Pixel sensors that react only to a change in value of a monitored pixel.

In some embodiments, said optical sensors comprise a group of Active Pixel sensors that generate output signals on a pixel-by-pixel basis in non-synchronous manner and only upon detecting a change in value of a particular pixel.

In some embodiments, said illumination sources generate InfraRed (IR) light having wavelength of 700 or more nanometers.

In some embodiments, said illumination sources generate Near InfraRed (NIR) light having wavelength of 700 to 1,200 nanometers.

In some embodiments, said illumination sources generate non-Infrared and non-NIR light, having wavelength of 1,200 or more nanometers.

In some embodiments, at least a first illumination source generates InfraRed (IR) light having wavelength of 700 or more nanometers; and at least a second illumination source concurrently generates Near InfraRed (NIR) light having wavelength of 700 to 1,200 nanometers; and at least a third illumination source concurrently generates non-Infrared and non-NIR light, having wavelength of 1,200 or more nanometers.

In some embodiments, said set of illumination sources are configured to selectively generate said illumination pulses with time intervals of up to 20 microseconds between two consecutive illumination sources.

In some embodiments, at least a first illumination source generates its illumination pulses at a first time-interval between pulses; and at least a second illumination source concurrently generates its illumination pulses at a second, different, time-interval between pulses.

In some embodiments, at least a first illumination source generates its illumination pulses at a first time-interval between pulses and at a first illumination wavelength; and at least a second illumination source concurrently generates its illumination pulses at a second, different, time-interval between pulses and at a second, different, illumination wavelength.

In some embodiments, at least a first illumination source generates its illumination pulses at a first time-interval between pulses and at a first illumination wavelength; and at least a second illumination source concurrently generates its illumination pulses at a second, different, time-interval between pulses and at a second, different, illumination wavelength; wherein an illumination modification controller causes selective modification of only the first time-interval and maintains the second time-interval unchanged.

In some embodiments, at least a first illumination source generates its illumination pulses at a first time-interval between pulses and at a first illumination wavelength; and at least a second illumination source concurrently generates its illumination pulses at a second, different, time-interval between pulses and at a second, different, illumination wavelength; wherein an illumination modification controller causes selective modification of only the first illumination wavelength and maintains the second illumination wavelength unchanged.

In some embodiments, at least a first illumination source generates its illumination pulses at a first time-interval between pulses and at a first illumination wavelength, and wherein said first illumination source is positioned to be directed towards a first region of said human eye; and at least a second illumination source concurrently generates its illumination pulses at a second, different, time-interval between pulses and at a second, different, illumination wavelength, and wherein said second illumination source is positioned to be directed towards a second region of said human eye; wherein an illumination modification controller causes selective modification of only the first time-interval and maintains the second time-interval unchanged.

In some embodiments, at least a first illumination source generates its illumination pulses at a first time-interval between pulses and at a first illumination wavelength, and wherein said first illumination source is positioned to be directed towards a first region of said human eye; at least a second illumination source concurrently generates its illumination pulses at a second, different, time-interval between pulses and at a second, different, illumination wavelength, and wherein said second illumination source is positioned to be directed towards a second region of said human eye; wherein an illumination modification controller causes selective modification of only the first illumination wavelength and maintains the second illumination wavelength unchanged.

In some embodiments, said optical sensors comprise self-calibrating Active Pixel sensors that are capable of self-calibration over time in response to changes in ambience or environment.

In some embodiments, said optical sensors comprise self-calibrating Active Pixel sensors that are capable of self-calibration of sensor sensitivity level in response to changes in ambience or environment.

In some embodiments, said optical sensors comprise Active Pixel sensors having a wide dynamic range of 110 db to 150 db.

In some embodiments, said optical sensors comprise Active Pixel sensors having a wide dynamic range of 130 db to 145 db.

In some embodiments, said optical sensors comprise Active Pixel sensors that transfer their output values to said processor in a non-synchronic manner and at non-pre-defined time intervals; wherein said processor operates to process signals received from said Active Pixel sensors in real-time or in near-real-time, without waiting to receive a full frame of pixels, and at non-pre-defined time intervals.

In some embodiments, said illumination sources comprise laser-based illumination sources that are capable of temporarily modifying their laser illumination wavelengths based on laser wavelength modification commands.

In some embodiments, said illumination sources comprise: at least one laser-based illumination source that is capable of temporarily modifying its laser illumination wavelength based on laser wavelength modification commands; and at least one LED-based or OLED-based illumination source that is capable of temporarily modifying its illumination wavelength based on wavelength modification commands.

In some embodiments, said system is a medical diagnostics system.

In some embodiments, said system is embedded within a helmet of a pilot or a head-gear wearable by a pilot.

In some embodiments, said system is embedded within an aircraft and is directed or aimed towards a general location or an estimated location of an eye of a pilot of said aircraft.

In some embodiments, said system is embedded within a vehicle and is directed towards a general location or an estimated location of an eye of a driver of said vehicle.

In some embodiments, said system is embedded within a gaming device and is directed or aimed towards a general location or an estimated location of an eye of a gaming user.

In some embodiments, said system is embedded within a smartphone or tablet or smart-watch or desktop computer or laptop computer, and is directed or aimed towards a general location or an estimated location of an eye of a user of such electronic device.

In some embodiments, an apparatus comprises: a set of illumination sources, to selectively generate illumination pulses towards an object-of-interest in accordance with a particular timing scheme per illumination source and in accordance with a particular wavelength per illumination source; a set of optical sensors, to sense changes to one or more properties of optical feedback reflected from the object-of-interest in response to modifications in operational properties of said set of illumination sources; a processor to process the sensed changes, and to generate one or more processing results that are based on said sensed changes.

Although portions of the discussion herein relate, for demonstrative purposes, to wired links and/or wired communications, some embodiments of the present invention are not limited in this regard, and may include one or more wired or wireless links, may utilize one or more components of wireless communication, may utilize one or more methods or protocols of wireless communication, or the like. Some embodiments may utilize wired communication and/or wireless communication, Wi-Fi communication, Bluetooth communication, Zigbee communication, cellular communication, wired transfer of signals (e.g., over a cable or wire), or the like.

The present invention may be implemented by using hardware units, software units, processors, CPUs, DSPs, integrated circuits, memory units, storage units, wireless communication modems or transmitters or receivers or transceivers, cellular transceivers, a power source, input units, output units, Operating System (OS), drivers, applications, and/or other suitable components.

The present invention may be implemented by using a neuromorphic processor or a neuromorphic machine or a special-purpose machine or a specific-purpose device that is not a generic computer, or by using a non-generic computer or a non-general computer or machine. Such system or device may utilize or may comprise one or more units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

The present invention may be implemented by using code or program code or machine-readable instructions or machine-readable code, which is stored on a non-transitory storage medium or non-transitory storage article (e.g., a CD-ROM, a DVD-ROM, a physical memory unit, a physical storage unit), such that the program or code or instructions, when executed by a processor or a machine or a computer, cause such device to perform a method in accordance with the present invention.

The present invention may enable machines and/or computerized systems to have new capabilities and/or new functions that were not available to such machines or systems so far; including, for example: a new capability to perform accurate, rapid and/or efficient tracking of eye or eye-components or ocular components, for one or more of the purposes described above.

Embodiments of the present invention may be utilized with a variety of devices or systems having a touch-screen or a touch-sensitive surface; for example, a smartphone, a cellular phone, a mobile phone, a smart-watch, a tablet, a handheld device, a portable electronic device, a portable gaming device, a portable audio/video player, an Augmented Reality (AR) device or headset or gear, a Virtual Reality (VR) device or headset or gear, a "kiosk" type device, a vending machine, an Automatic Teller Machine (ATM), a camera, a three-dimensional camera, a camera for capturing 3D data or images or video, a stereoscopic camera or imager, a laptop computer, a desktop computer, a vehicular computer, a vehicular dashboard, a vehicular touch-screen, or the like.

The system(s) and/or device(s) of the present invention may optionally comprise, or may be implemented by utilizing suitable hardware components and/or software components; for example, processors, processor cores, Central Processing Units (CPUs), Digital Signal Processors (DSPs), circuits, Integrated Circuits (ICs), controllers, memory units, registers, accumulators, storage units, input units (e.g., touch-screen, keyboard, keypad, stylus, mouse, touchpad, joystick, trackball, microphones), output units (e.g., screen, touch-screen, monitor, display unit, audio speakers), acoustic microphone(s) and/or sensor(s), optical microphone(s) and/or sensor(s), laser or laser-based microphone(s) and/or sensor(s), wired or wireless modems or transceivers or transmitters or receivers, GPS receiver or GPS element or other location-based or location-determining unit or system, network elements (e.g., routers, switches, hubs, antennas), and/or other suitable components and/or modules.

The system(s) and/or devices of the present invention may optionally be implemented by utilizing co-located components, remote components or modules, "cloud computing" servers or devices or storage, client/server architecture, peer-to-peer architecture, distributed architecture, and/or other suitable architectures or system topologies or network topologies.

In accordance with embodiments of the present invention, calculations, operations and/or determinations may be performed locally within a single device, or may be performed by or across multiple devices, or may be performed partially locally and partially remotely (e.g., at a remote server) by optionally utilizing a communication channel to exchange raw data and/or processed data and/or processing results.

Some embodiments may be implemented by using a special-purpose machine or a specific-purpose device that is not a generic computer, or by using a non-generic computer or a non-general computer or machine. Such system or device may utilize or may comprise one or more components or units or modules that are not part of a "generic computer" and that are not part of a "general purpose computer", for example, cellular transceivers, cellular transmitter, cellular receiver, GPS unit, location-determining unit, accelerometer(s), gyroscope(s), device-orientation detectors or sensors, device-positioning detectors or sensors, or the like.

Some embodiments may be implemented as, or by utilizing, an automated method or automated process, or a machine-implemented method or process, or as a semi-automated or partially-automated method or process, or as a set of steps or operations which may be executed or performed by a computer or machine or system or other device.

Some embodiments may be implemented by using code or program code or machine-readable instructions or machine-readable code, which may be stored on a non-transitory storage medium or non-transitory storage article (e.g., a CD-ROM, a DVD-ROM, a physical memory unit, a physical storage unit), such that the program or code or instructions, when executed by a processor or a machine or a computer, cause such processor or machine or computer to perform a method or process as described herein. Such code or instructions may be or may comprise, for example, one or more of: software, a software module, an application, a program, a subroutine, instructions, an instruction set, computing code, words, values, symbols, strings, variables, source code, compiled code, interpreted code, executable code, static code, dynamic code; including (but not limited to) code or instructions in high-level programming language, low-level programming language, object-oriented programming language, visual programming language, compiled programming language, interpreted programming language, C, C++, C#, Java, JavaScript, SQL, Ruby on Rails, Go, Cobol, Fortran, ActionScript, AJAX, XML, JSON, Lisp, Eiffel, Verilog, Hardware Description Language (HDL, BASIC, Visual BASIC, Matlab, Pascal, HTML, HTML5, CSS, Perl, Python, PHP, machine language, machine code, assembly language, or the like.

Discussions herein utilizing terms such as, for example, "processing", "computing", "calculating", "determining", "establishing", "analyzing", "checking", "detecting", "measuring", or the like, may refer to operation(s) and/or process(es) of a processor, a computer, a computing platform, a computing system, or other electronic device or computing device, that may automatically and/or autonomously manipulate and/or transform data represented as physical (e.g., electronic) quantities within registers and/or accumulators and/or memory units and/or storage units into other data or that may perform other suitable operations.

Some embodiments of the present invention may perform steps or operations such as, for example, "determining", "identifying", "comparing", "checking", "querying", "searching", "matching", and/or "analyzing", by utilizing, for example: a pre-defined threshold value to which one or more parameter values may be compared; a comparison between (i) sensed or measured or calculated value(s), and (ii) pre-defined or dynamically-generated threshold value(s) and/or range values and/or upper limit value and/or lower limit value and/or maximum value and/or minimum value; a comparison or matching between sensed or measured or calculated data, and one or more values as stored in a look-up table or a legend table or a list of reference value(s) or a database of reference values or ranges; a comparison or matching or searching process which searches for matches and/or identical results and/or similar results and/or sufficiently-close results, among multiple values or limits that are stored in a database or look-up table; utilization of one or more equations, formula, weighted formula, and/or other calculation in order to determine similarity or a match between or among parameters or values; utilization of comparator units, lookup tables, threshold values, conditions, conditioning logic, Boolean operator(s) and/or other suitable components and/or operations.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments", "some embodiments", and/or similar terms, may indicate that the embodiment(s) so described may optionally include a particular feature, structure, or characteristic, but not every embodiment necessarily includes the particular feature, structure, or characteristic. Repeated use of the phrase "in one embodiment" does not necessarily refer to the same embodiment, although it may. Repeated use of the phrase "in some embodiments" does not necessarily refer to the same set or group of embodiments, although it may.

As used herein, and unless otherwise specified, the utilization of ordinal adjectives such as "first", "second", "third", "fourth", and so forth, to describe an item or an object, merely indicates that different instances of such like items or objects are being referred to; and does not intend to imply as if the items or objects so described must be in a particular given sequence, either temporally, spatially, in ranking, or in any other ordering manner.

Some embodiments may comprise, or may be implemented by using, an "app" or application which may be downloaded or obtained from an "app store" or "applications store", for free or for a fee, or which may be pre-installed on a computing device or electronic device, or which may be transported to and/or installed on such computing device or electronic device.

In some embodiments, a method comprises: (a) monitoring user interactions of a user that Functions, operations, components and/or features described herein with reference to one or more embodiments of the present invention, may be combined with, or may be utilized in combination with, one or more other functions, operations, components and/or features described herein with reference to one or more other embodiments of the present invention. The present invention may comprise any possible combinations, re-arrangements, assembly, re-assembly, or other utilization of some or all of the modules or functions or components that are described herein, even if they are discussed in different locations or different chapters of the above discussion, or even if they are shown across different drawings or multiple drawings, or even if they are depicted in any drawing(s) without necessarily being connected via a line or an arrow.

While certain features of the present invention have been illustrated and described herein, many modifications, substitutions, changes, and equivalents may occur to those skilled in the art. Accordingly, the claims are intended to cover all such modifications, substitutions, changes, and equivalents.

What is claimed is:

1. A system comprising:
   (a) a set of illumination sources, to selectively generate illumination pulses of Near InfraRed (NIR) light having wavelength of 700 to 1,200 nanometers, at time intervals of up to 20 microseconds between two consecutive illumination pulses, towards a human eye, in accordance with a particular timing scheme per illumination source and in accordance with a particular wavelength per illumination source;
   (b) a set of optical sensors, to sense changes to one or more properties of reflections of said illumination pulses from the human eye in response to modifications in operational properties of said set of illumination sources;
   wherein said optical sensors comprise a group of Active Pixel sensors, that react only to a change in value of a monitored pixel, and that generate output signals on a pixel-by-pixel basis in non-synchronous manner and only upon detecting a change in value of a particular pixel;
   (c) a processor to process the sensed changes as represented by the output of said Active Pixel sensors, and to generate one or more processing results that are based on said sensed changes,
   wherein said Active Pixel sensors are configured to transfer their output values to said processor in a non-synchronic manner and at non-pre-defined time intervals;
   wherein said processor is configured to process signals received from said Active Pixel sensors in real-time or in near-real-time, without waiting to receive a full frame of pixels, and at non-pre-defined time intervals.

2. The system of claim 1,
   wherein said optical sensors are configured to exclusively sense and to be responsive only to changes in reflections from an object within the field-of-view of the optical sensors.

3. The system of claim 1,
   wherein the processor generates said processing results by taking into account also
   (i) known spatial distances between the illumination sources and said human eye, and
   (ii) known spatial distances between the optical sensors and said human eye.

4. The system of claim 1, further comprising:
   an oscillation controller to cause selective spatial oscillation of said illumination sources;
   wherein the processor generates said processing results by taking into account said selective spatial oscillation of said illumination sources.

5. The system of claim 1, further comprising:
   a vibration controller to cause selective spatial vibration of said illumination sources;

wherein the processor generates said processing results by taking into account said selective spatial vibration of said illumination sources.

6. The system of claim 1, further comprising:
a motion controller to cause selective spatial motion of said illumination sources;
wherein the processor generates said processing results by taking into account said selective spatial motion of said illumination sources.

7. The system of claim 1, further comprising:
a wavelength modification controller, to cause selective modification of wavelength of only some but not all of said illumination sources;
wherein the processor generates said processing results by taking into account said selective modification of wavelength of only some but not all of said illumination sources.

8. The system of claim 1, further comprising:
a wavelength modification controller, (i) to cause a first illumination source and a second illumination source to illuminate at a same particular wavelength, and (ii) to cause selective modification of the wavelength of illumination of the first illumination source while maintaining the wavelength of illumination of the second illumination source;
wherein the processor generates said processing results by taking into account said selective modification of wavelength.

9. The system of claim 1, further comprising:
a wavelength modification controller, (i) to cause a first illumination source to illuminate at a first wavelength, and (ii) to cause a second illumination source to illuminate at a second wavelength, and (iii) to cause selective modification of the wavelength of illumination of the first illumination source while maintaining the wavelength of illumination of the second illumination source;
wherein the processor generates said processing results by taking into account said selective modification of wavelength.

10. The system of claim 1, further comprising:
a wavelength modification controller, to cause modification of wavelength of all of said illumination sources in accordance with a particular timing scheme;
wherein the processor generates said processing results by taking into account said selective modification of wavelength of and said particular timing scheme.

11. The system of claim 1,
wherein said illumination sources comprise LED-based or OLED-based illumination sources that are capable of temporarily modifying their illumination wavelengths based on wavelength modification commands.

12. The system of claim 1,
wherein said illumination sources generate InfraRed (IR) light having wavelength of 700 or more nanometers.

13. The system of claim 1,
wherein said illumination sources generate non-Infrared and non-NIR light, having wavelength of 1,200 or more nanometers.

14. The system of claim 1,
wherein at least a first illumination source generates InfraRed (IR) light having wavelength of 700 or more nanometers;
wherein at least a second illumination source concurrently generates Near InfraRed (NIR) light having wavelength of 700 to 1,200 nanometers;
wherein at least a third illumination source concurrently generates non-Infrared and non-NIR light, having wavelength of 1,200 or more nanometers.

15. The system of claim 1,
wherein at least a first illumination source generates its illumination pulses at a first time-interval between pulses;
wherein at least a second illumination source concurrently generates its illumination pulses at a second, different, time-interval between pulses.

16. The system of claim 1,
wherein at least a first illumination source generates its illumination pulses at a first time-interval between pulses and at a first illumination wavelength;
wherein at least a second illumination source concurrently generates its illumination pulses at a second, different, time-interval between pulses and at a second, different, illumination wavelength.

17. The system of claim 1,
wherein at least a first illumination source generates its illumination pulses at a first time-interval between pulses and at a first illumination wavelength;
wherein at least a second illumination source concurrently generates its illumination pulses at a second, different, time-interval between pulses and at a second, different, illumination wavelength;
wherein an illumination modification controller causes selective modification of only the first time-interval and maintains the second time-interval unchanged.

18. The system of claim 1,
wherein at least a first illumination source generates its illumination pulses at a first time-interval between pulses and at a first illumination wavelength;
wherein at least a second illumination source concurrently generates its illumination pulses at a second, different, time-interval between pulses and at a second, different, illumination wavelength;
wherein an illumination modification controller causes selective modification of only the first illumination wavelength and maintains the second illumination wavelength unchanged.

19. The system of claim 1,
wherein at least a first illumination source generates its illumination pulses at a first time-interval between pulses and at a first illumination wavelength, and wherein said first illumination source is positioned to be directed towards a first region of said human eye;
wherein at least a second illumination source concurrently generates its illumination pulses at a second, different, time-interval between pulses and at a second, different, illumination wavelength, and wherein said second illumination source is positioned to be directed towards a second region of said human eye;
wherein an illumination modification controller causes selective modification of only the first time-interval and maintains the second time-interval unchanged.

20. The system of claim 1,
wherein at least a first illumination source generates its illumination pulses at a first time-interval between pulses and at a first illumination wavelength, and wherein said first illumination source is positioned to be directed towards a first region of said human eye;

wherein at least a second illumination source concurrently generates its illumination pulses at a second, different, time-interval between pulses and at a second, different, illumination wavelength, and wherein said second illumination source is positioned to be directed towards a second region of said human eye;

wherein an illumination modification controller causes selective modification of only the first illumination wavelength and maintains the second illumination wavelength unchanged.

21. The system of claim 1,
wherein said optical sensors comprise self-calibrating Active Pixel sensors that are capable of self-calibration over time in response to changes in ambience or environment.

22. The system of claim 1,
wherein said optical sensors comprise self-calibrating Active Pixel sensors that are capable of self-calibration of sensor sensitivity level in response to changes in ambience or environment.

23. The system of claim 1,
wherein said optical sensors comprise Active Pixel sensors having a wide dynamic range of 110 db to 150 db.

24. The system of claim 1,
wherein said optical sensors comprise Active Pixel sensors having a wide dynamic range of 130 db to 145 db.

25. The system of claim 1,
wherein said illumination sources comprise laser-based illumination sources that are capable of temporarily modifying their laser illumination wavelengths based on laser wavelength modification commands.

26. The system of claim 1,
wherein said illumination sources comprise:
at least one laser-based illumination source that is capable of temporarily modifying its laser illumination wavelength based on laser wavelength modification commands; and
at least one LED-based or OLED-based illumination source that is capable of temporarily modifying its illumination wavelength based on wavelength modification commands.

27. The system of claim 1,
wherein said system is a medical diagnostics system.

28. The system of claim 1,
wherein said system is embedded within a helmet of a pilot or a head-gear wearable by a pilot.

29. The system of claim 1,
wherein said system is embedded within an aircraft and is directed towards a general location of an eye of a pilot of said aircraft.

30. The system of claim 1,
wherein said system is embedded within a vehicle and is directed towards a general location of an eye of a driver of said vehicle.

31. The system of claim 1,
wherein said system is embedded within a gaming device and is directed towards a general location of an eye of a gaming user.

32. The system of claim 1,
wherein said system is embedded within an electronic device selected from the group consisting of: a smartphone, a tablet, a smart-watch, a desktop computer, a laptop computer; wherein the system is directed towards a general location of an eye of a user of said electronic device.

\* \* \* \* \*